United States Patent
Ernst et al.

(10) Patent No.: US 9,943,247 B2
(45) Date of Patent: Apr. 17, 2018

(54) SYSTEMS, DEVICES, AND METHODS FOR DETECTING FALSE MOVEMENTS FOR MOTION CORRECTION DURING A MEDICAL IMAGING SCAN

(71) Applicants: The University of Hawai'i, Honolulu, HI (US); The Queen's Medical Center, Honolulu, HI (US)

(72) Inventors: Thomas Michael Ernst, Honolulu, HI (US); Brian Keating, Honolulu, HI (US); Aditya Singh, Honolulu, HI (US); Maxim Zaitsev, Freiburg (DE); Michael Herbst, Freiburg (DE)

(73) Assignees: The University of Hawai'i, Honolulu, HI (US); The Queen's Medical Center, Honolulu, HI (US)

( * ) Notice: Subject to any disclaimer, the term of this patent is extended or adjusted under 35 U.S.C. 154(b) by 44 days.

(21) Appl. No.: 15/222,811

(22) Filed: Jul. 28, 2016

(65) Prior Publication Data
US 2017/0032538 A1  Feb. 2, 2017

Related U.S. Application Data

(60) Provisional application No. 62/198,079, filed on Jul. 28, 2015.

(51) Int. Cl.
*G06K 9/00* (2006.01)
*A61B 5/055* (2006.01)
(Continued)

(52) U.S. Cl.
CPC ............ *A61B 5/055* (2013.01); *A61B 5/1121* (2013.01); *A61B 5/1127* (2013.01); *A61B 5/682* (2013.01);
(Continued)

(58) Field of Classification Search
USPC ........ 382/103, 104, 155, 203; 345/156, 168; 375/240.01, 240.09; 701/45; 715/863
See application file for complete search history.

(56) References Cited

U.S. PATENT DOCUMENTS 3,811,213 A   5/1974 Eaves
4,689,999 A   9/1987 Shkedi
(Continued)

FOREIGN PATENT DOCUMENTS

CN   105392423   3/2016
DE   29519078    3/1996
(Continued)

OTHER PUBLICATIONS

Armstrong et al., RGR-6D: Low-cost, high-accuracy measurement of 6-DOF Pose from a Single Image. Publication date unknown.
(Continued)

*Primary Examiner* — Anh H Do
(74) *Attorney, Agent, or Firm* — Knobbe, Martens, Olson & Bear LLP

(57) ABSTRACT

The systems, methods, and devices described herein generally relate to achieving accurate and robust motion correction by detecting and accounting for false movements in motion correction systems used in conjunction with medical imaging and/or therapeutic systems. In other words, in some embodiments of the systems, methods, and devices described herein can be configured to detect false movements for motion correction during a medical imaging scan and/or therapeutic procedure, and thereby ensure that such false movements are not accounted for in the motion correction process. Upon detection of false movements, the imaging or therapeutic system can be configured to transiently suppress and/or subsequently repeat acquisitions.

14 Claims, 11 Drawing Sheets

(51) Int. Cl.
  *G06K 9/62* (2006.01)
  *G06K 9/66* (2006.01)
  *G06T 7/00* (2017.01)
  *A61B 5/00* (2006.01)
  *G06T 7/246* (2017.01)
  *A61B 5/11* (2006.01)

(52) U.S. Cl.
  CPC .......... *A61B 5/7207* (2013.01); *A61B 5/7267* (2013.01); *G06K 9/6256* (2013.01); *G06K 9/6277* (2013.01); *G06K 9/66* (2013.01); *G06T 7/0012* (2013.01); *G06T 7/248* (2017.01); *G06T 2207/10016* (2013.01); *G06T 2207/20081* (2013.01); *G06T 2207/30204* (2013.01)

(56) References Cited

U.S. PATENT DOCUMENTS

| | | |
|---|---|---|
| 4,724,386 A | 2/1988 | Haacke et al. |
| 4,894,129 A | 1/1990 | Leiponen et al. |
| 4,923,295 A | 5/1990 | Sireul et al. |
| 4,953,554 A | 9/1990 | Zerhouni et al. |
| 4,988,886 A | 1/1991 | Palum et al. |
| 5,075,562 A | 12/1991 | Greivenkamp et al. |
| 5,318,026 A | 6/1994 | Pelc |
| 5,515,711 A | 5/1996 | Hinkle |
| 5,545,993 A | 8/1996 | Taguchi et al. |
| 5,615,677 A | 4/1997 | Pelc et al. |
| 5,687,725 A | 11/1997 | Wendt |
| 5,728,935 A | 3/1998 | Czompo |
| 5,802,202 A | 9/1998 | Yamada et al. |
| 5,835,223 A | 11/1998 | Zawemer et al. |
| 5,886,257 A | 3/1999 | Gustafson et al. |
| 5,889,505 A | 3/1999 | Toyama |
| 5,936,722 A | 8/1999 | Armstrong et al. |
| 5,936,723 A | 8/1999 | Schmidt et al. |
| 5,947,900 A | 9/1999 | Derbyshire et al. |
| 5,987,349 A | 11/1999 | Schulz |
| 6,031,888 A | 2/2000 | Ivan et al. |
| 6,044,308 A | 3/2000 | Huissoon |
| 6,057,680 A | 5/2000 | Foo et al. |
| 6,061,644 A | 5/2000 | Leis |
| 6,088,482 A | 7/2000 | He |
| 6,144,875 A | 11/2000 | Schweikard et al. |
| 6,236,737 B1 | 5/2001 | Gregson et al. |
| 6,246,900 B1 | 6/2001 | Cosman et al. |
| 6,279,579 B1 | 8/2001 | Riaziat et al. |
| 6,285,902 B1 | 9/2001 | Kienzle, III et al. |
| 6,289,235 B1 | 9/2001 | Webber |
| 6,292,683 B1 | 9/2001 | Gupta et al. |
| 6,298,262 B1 | 10/2001 | Franck et al. |
| 6,381,485 B1 | 4/2002 | Hunter et al. |
| 6,384,908 B1 | 5/2002 | Schmidt et al. |
| 6,390,982 B1 | 5/2002 | Bova et al. |
| 6,402,762 B2 | 6/2002 | Hunter et al. |
| 6,405,072 B1 | 6/2002 | Cosman |
| 6,421,551 B1 | 7/2002 | Kuth et al. |
| 6,467,905 B1 | 10/2002 | Stahl et al. |
| 6,474,159 B1 | 11/2002 | Foxlin et al. |
| 6,484,131 B1 | 11/2002 | Amoral-Moriya et al. |
| 6,490,475 B1 | 12/2002 | Seeley et al. |
| 6,501,981 B1 | 12/2002 | Schweikard et al. |
| 6,587,707 B2 | 7/2003 | Nehrke et al. |
| 6,621,889 B1 | 9/2003 | Mostafavi |
| 6,650,920 B2 | 11/2003 | Schaldach et al. |
| 6,662,036 B2 | 12/2003 | Cosman |
| 6,687,528 B2 | 2/2004 | Gupta et al. |
| 6,690,965 B1 | 2/2004 | Riaziat et al. |
| 6,711,431 B2 | 3/2004 | Sarin et al. |
| 6,731,970 B2 | 5/2004 | Schlossbauer et al. |
| 6,758,218 B2 | 7/2004 | Anthony |
| 6,771,997 B2 | 8/2004 | Schaffer |
| 6,794,869 B2 | 9/2004 | Brittain |
| 6,856,827 B2 | 2/2005 | Seeley et al. |
| 6,856,828 B2 | 2/2005 | Cossette et al. |
| 6,876,198 B2 | 4/2005 | Watanabe et al. |
| 6,888,924 B2 | 5/2005 | Claus et al. |
| 6,891,374 B2 | 5/2005 | Brittain |
| 6,892,089 B1 | 5/2005 | Prince et al. |
| 6,897,655 B2 | 5/2005 | Brittain et al. |
| 6,913,603 B2 | 7/2005 | Knopp et al. |
| 6,937,696 B1 | 8/2005 | Mostafavi |
| 6,959,266 B1 | 10/2005 | Mostafavi |
| 6,973,202 B2 | 12/2005 | Mostafavi |
| 6,980,679 B2 | 12/2005 | Jeung et al. |
| 7,007,699 B2 | 3/2006 | Martinelli et al. |
| 7,107,091 B2 | 9/2006 | Jutras et al. |
| 7,110,805 B2 | 9/2006 | Machida |
| 7,123,758 B2 | 10/2006 | Jeung et al. |
| 7,171,257 B2 | 1/2007 | Thomson |
| 7,176,440 B2 | 2/2007 | Cofer et al. |
| 7,191,100 B2 | 3/2007 | Mostafavi |
| 7,204,254 B2 | 4/2007 | Riaziat et al. |
| 7,209,777 B2 | 4/2007 | Saranathan et al. |
| 7,209,977 B2 | 4/2007 | Acharya et al. |
| 7,260,253 B2 | 8/2007 | Rahn et al. |
| 7,260,426 B2 | 8/2007 | Schweikard et al. |
| 7,295,007 B2 | 11/2007 | Dold |
| 7,313,430 B2 | 12/2007 | Urquhart et al. |
| 7,327,865 B2 | 2/2008 | Fu et al. |
| 7,348,776 B1 | 3/2008 | Aksoy et al. |
| 7,403,638 B2 | 7/2008 | Jeung et al. |
| 7,494,277 B2 | 2/2009 | Setala |
| 7,498,811 B2 | 3/2009 | Macfarlane et al. |
| 7,502,413 B2 * | 3/2009 | Robert ............... H04N 19/543 375/240.01 |
| 7,505,805 B2 | 3/2009 | Kuroda |
| 7,535,411 B2 | 5/2009 | Falco |
| 7,551,089 B2 | 6/2009 | Sawyer |
| 7,561,909 B1 | 7/2009 | Pai et al. |
| 7,567,697 B2 | 7/2009 | Mostafavi |
| 7,573,269 B2 | 8/2009 | Yao |
| 7,602,301 B1 | 10/2009 | Stirling et al. |
| 7,603,155 B2 | 10/2009 | Jensen |
| 7,623,623 B2 | 11/2009 | Raanes et al. |
| 7,657,300 B2 | 2/2010 | Hunter et al. |
| 7,657,301 B2 | 2/2010 | Mate et al. |
| 7,659,521 B2 | 2/2010 | Pedroni |
| 7,660,623 B2 | 2/2010 | Hunter et al. |
| 7,668,288 B2 | 2/2010 | Conwell et al. |
| 7,689,263 B1 | 3/2010 | Fung et al. |
| 7,702,380 B1 | 4/2010 | Dean |
| 7,715,604 B2 | 5/2010 | Sun et al. |
| 7,742,077 B2 | 6/2010 | Sablak et al. |
| 7,742,621 B2 | 6/2010 | Hammoud et al. |
| 7,742,804 B2 | 6/2010 | Faul et al. |
| 7,744,528 B2 | 6/2010 | Wallace et al. |
| 7,760,908 B2 | 7/2010 | Curtner et al. |
| 7,766,837 B2 | 8/2010 | Pedrizzetti et al. |
| 7,769,430 B2 | 8/2010 | Mostafavi |
| 7,772,569 B2 | 8/2010 | Bewersdorf et al. |
| 7,787,011 B2 | 8/2010 | Zhou et al. |
| 7,787,935 B2 | 8/2010 | Dumoulin et al. |
| 7,791,808 B2 | 9/2010 | French et al. |
| 7,792,249 B2 | 9/2010 | Gertner et al. |
| 7,796,154 B2 | 9/2010 | Senior et al. |
| 7,798,730 B2 | 9/2010 | Westerweck |
| 7,801,330 B2 | 9/2010 | Zhang et al. |
| 7,805,987 B1 | 10/2010 | Smith |
| 7,806,604 B2 | 10/2010 | Bazakos et al. |
| 7,817,046 B2 | 10/2010 | Coveley et al. |
| 7,817,824 B2 | 10/2010 | Liang et al. |
| 7,819,818 B2 | 10/2010 | Ghajar |
| 7,833,221 B2 | 11/2010 | Voegele |
| 7,834,846 B1 | 11/2010 | Bell |
| 7,835,783 B1 | 11/2010 | Aletras |
| 7,839,551 B2 | 11/2010 | Lee et al. |
| 7,840,253 B2 | 11/2010 | Tremblay et al. |
| 7,844,094 B2 | 11/2010 | Jeung et al. |
| 7,844,320 B2 | 11/2010 | Shahidi |
| 7,850,526 B2 | 12/2010 | Zalewski et al. |
| 7,860,301 B2 | 12/2010 | Se et al. |
| 7,866,818 B2 | 1/2011 | Schroeder et al. |

(56) References Cited

U.S. PATENT DOCUMENTS

| | | | |
|---|---|---|---|
| 7,868,282 B2 | 1/2011 | Lee et al. |
| 7,878,652 B2 | 2/2011 | Chen et al. |
| 7,883,415 B2 | 2/2011 | Larsen et al. |
| 7,889,907 B2 | 2/2011 | Engelbart et al. |
| 7,894,877 B2 | 2/2011 | Lewin et al. |
| 7,902,825 B2 | 3/2011 | Bammer et al. |
| 7,907,987 B2 | 3/2011 | Dempsey |
| 7,908,060 B2 | 3/2011 | Basson et al. |
| 7,908,233 B2 | 3/2011 | Angell et al. |
| 7,911,207 B2 | 3/2011 | Macfarlane et al. |
| 7,912,532 B2 | 3/2011 | Schmidt et al. |
| 7,920,250 B2 | 4/2011 | Robert et al. |
| 7,920,911 B2 | 4/2011 | Hoshino et al. |
| 7,925,066 B2 | 4/2011 | Ruohonen et al. |
| 7,925,549 B2 | 4/2011 | Looney et al. |
| 7,931,370 B2 | 4/2011 | Prat Bartomeu |
| 7,944,354 B2 | 5/2011 | Kangas et al. |
| 7,944,454 B2 | 5/2011 | Zhou et al. |
| 7,945,304 B2 | 5/2011 | Feinberg |
| 7,946,921 B2 | 5/2011 | Ofek et al. |
| 7,962,197 B2 | 6/2011 | Rioux et al. |
| 7,971,999 B2 | 7/2011 | Zinser |
| 7,977,942 B2 | 7/2011 | White |
| 7,978,925 B1 | 7/2011 | Souchard |
| 7,988,288 B2 | 8/2011 | Donaldson |
| 7,990,365 B2 | 8/2011 | Marvit et al. |
| 8,005,571 B2 | 8/2011 | Sutherland et al. |
| 8,009,198 B2 | 8/2011 | Alhadef |
| 8,019,170 B2 | 9/2011 | Wang et al. |
| 8,021,231 B2 | 9/2011 | Walker et al. |
| 8,022,982 B2 | 9/2011 | Thorn |
| 8,024,026 B2 | 9/2011 | Groszmann |
| 8,031,909 B2 | 10/2011 | Se et al. |
| 8,031,933 B2 | 10/2011 | Se et al. |
| 8,036,425 B2 | 10/2011 | Hou |
| 8,041,077 B2 | 10/2011 | Bell |
| 8,041,412 B2 | 10/2011 | Glossop et al. |
| 8,048,002 B2 | 11/2011 | Ghajar |
| 8,049,867 B2 | 11/2011 | Bridges et al. |
| 8,055,020 B2 | 11/2011 | Meuter et al. |
| 8,055,049 B2 | 11/2011 | Stayman et al. |
| 8,060,185 B2 | 11/2011 | Hunter et al. |
| 8,063,929 B2 | 11/2011 | Kurtz et al. |
| 8,073,197 B2 | 12/2011 | Xu et al. |
| 8,077,914 B1 | 12/2011 | Kaplan |
| 8,085,302 B2 | 12/2011 | Zhang et al. |
| 8,086,026 B2 | 12/2011 | Schulz |
| 8,086,299 B2 | 12/2011 | Adler et al. |
| RE43,147 E | 1/2012 | Aviv |
| 8,094,193 B2 | 1/2012 | Peterson |
| 8,095,203 B2 | 1/2012 | Wright et al. |
| 8,095,209 B2 | 1/2012 | Flaherty |
| 8,098,889 B2 | 1/2012 | Zhu et al. |
| 8,113,991 B2 | 2/2012 | Kutliroff |
| 8,116,527 B2 | 2/2012 | Sabol |
| 8,121,356 B2 | 2/2012 | Friedman |
| 8,121,361 B2 | 2/2012 | Ernst et al. |
| 8,134,597 B2 | 3/2012 | Thorn |
| 8,135,201 B2 | 3/2012 | Smith et al. |
| 8,139,029 B2 | 3/2012 | Boillot |
| 8,139,896 B1 | 3/2012 | Ahiska |
| 8,144,118 B2 | 3/2012 | Hildreth |
| 8,144,148 B2 | 3/2012 | El Dokor |
| 8,150,063 B2 | 4/2012 | Chen |
| 8,150,498 B2 | 4/2012 | Gielen et al. |
| 8,160,304 B2 | 4/2012 | Rhoads |
| 8,165,844 B2 | 4/2012 | Luinge et al. |
| 8,167,802 B2 | 5/2012 | Baba et al. |
| 8,172,573 B2 | 5/2012 | Sonenfeld et al. |
| 8,175,332 B2 | 5/2012 | Harrington |
| 8,179,604 B1 | 5/2012 | Prada Gomez et al. |
| 8,180,428 B2 | 5/2012 | Kaiser et al. |
| 8,180,432 B2 | 5/2012 | Sayeh |
| 8,187,097 B1 | 5/2012 | Zhang |
| 8,189,869 B2 | 5/2012 | Bell |
| 8,189,889 B2 | 5/2012 | Pearlstein et al. |
| 8,189,926 B2 | 5/2012 | Sharma |
| 8,190,233 B2 | 5/2012 | Dempsey |
| 8,191,359 B2 | 6/2012 | White et al. |
| 8,194,134 B2 | 6/2012 | Furukawa |
| 8,195,084 B2 | 6/2012 | Xiao |
| 8,199,983 B2 | 6/2012 | Qureshi |
| 8,206,219 B2 | 6/2012 | Shum |
| 8,207,967 B1 | 6/2012 | El Dokor |
| 8,208,758 B2 | 6/2012 | Wang |
| 8,213,693 B1 | 7/2012 | Li |
| 8,214,012 B2 | 7/2012 | Zuccolotto et al. |
| 8,214,016 B2 | 7/2012 | Lavallee et al. |
| 8,216,016 B2 | 7/2012 | Yamagishi et al. |
| 8,218,818 B2 | 7/2012 | Cobb |
| 8,218,819 B2 | 7/2012 | Cobb |
| 8,218,825 B2 | 7/2012 | Gordon |
| 8,221,399 B2 | 7/2012 | Amano |
| 8,223,147 B1 | 7/2012 | El Dokor |
| 8,224,423 B2 | 7/2012 | Faul |
| 8,226,574 B2 | 7/2012 | Whillock |
| 8,229,163 B2 | 7/2012 | Coleman |
| 8,229,166 B2 | 7/2012 | Teng |
| 8,229,184 B2 | 7/2012 | Benkley |
| 8,232,872 B2 | 7/2012 | Zeng |
| 8,235,529 B1 | 8/2012 | Raffle |
| 8,235,530 B2 | 8/2012 | Maad |
| 8,241,125 B2 | 8/2012 | Hughes |
| 8,243,136 B2 | 8/2012 | Aota |
| 8,243,269 B2 | 8/2012 | Matousek |
| 8,243,996 B2 | 8/2012 | Steinberg |
| 8,248,372 B2 | 8/2012 | Saila |
| 8,249,691 B2 | 8/2012 | Chase et al. |
| 8,253,770 B2 | 8/2012 | Kurtz |
| 8,253,774 B2 | 8/2012 | Huitema |
| 8,253,778 B2 | 8/2012 | Atsushi |
| 8,259,109 B2 | 9/2012 | El Dokor |
| 8,260,036 B2 | 9/2012 | Hamza et al. |
| 8,279,288 B2 | 10/2012 | Son |
| 8,284,157 B2 | 10/2012 | Markovic |
| 8,284,847 B2 | 10/2012 | Adermann |
| 8,287,373 B2 | 10/2012 | Marks et al. |
| 8,289,390 B2 | 10/2012 | Aggarwal |
| 8,289,392 B2 | 10/2012 | Senior et al. |
| 8,290,208 B2 | 10/2012 | Kurtz |
| 8,290,229 B2 | 10/2012 | Qureshi |
| 8,295,573 B2 | 10/2012 | Bredno et al. |
| 8,301,226 B2 | 10/2012 | Csavoy et al. |
| 8,306,260 B2 | 11/2012 | Zhu |
| 8,306,267 B1 | 11/2012 | Gossweiler, III |
| 8,306,274 B2 | 11/2012 | Grycewicz |
| 8,306,663 B2 | 11/2012 | Wickham |
| 8,310,656 B2 | 11/2012 | Zalewski |
| 8,310,662 B2 | 11/2012 | Mehr |
| 8,311,611 B2 | 11/2012 | Csavoy et al. |
| 8,314,854 B2 | 11/2012 | Yoon |
| 8,315,691 B2 | 11/2012 | Sumanaweera et al. |
| 8,316,324 B2 | 11/2012 | Boillot |
| 8,320,621 B2 | 11/2012 | McEldowney |
| 8,320,709 B2 | 11/2012 | Arartani et al. |
| 8,323,106 B2 | 12/2012 | Zalewski |
| 8,325,228 B2 | 12/2012 | Mariadoss |
| 8,330,811 B2 | 12/2012 | Macguire, Jr. |
| 8,330,812 B2 | 12/2012 | Maguire, Jr. |
| 8,331,019 B2 | 12/2012 | Cheong |
| 8,334,900 B2 | 12/2012 | Qu et al. |
| 8,339,282 B2 | 12/2012 | Noble |
| 8,351,651 B2 | 1/2013 | Lee |
| 8,368,586 B2 | 2/2013 | Mohamadi |
| 8,369,574 B2 | 2/2013 | Hu |
| 8,374,393 B2 | 2/2013 | Cobb |
| 8,374,411 B2 | 2/2013 | Ernst et al. |
| 8,374,674 B2 | 2/2013 | Gertner |
| 8,376,226 B2 | 2/2013 | Dennard |
| 8,376,827 B2 | 2/2013 | Cammegh |
| 8,379,927 B2 | 2/2013 | Taylor |
| 8,380,284 B2 | 2/2013 | Saranathan et al. |
| 8,386,011 B2 | 2/2013 | Wieczorek |
| 8,390,291 B2 | 3/2013 | Macfarlane et al. |

(56) References Cited

U.S. PATENT DOCUMENTS

| | | |
|---|---|---|
| 8,390,729 B2 | 3/2013 | Long |
| 8,395,620 B2 | 3/2013 | El Dokor |
| 8,396,654 B1 | 3/2013 | Simmons et al. |
| 8,400,398 B2 | 3/2013 | Schoen |
| 8,400,490 B2 | 3/2013 | Apostolopoulos |
| 8,405,491 B2 | 3/2013 | Fong |
| 8,405,656 B2 | 3/2013 | El Dokor |
| 8,405,717 B2 | 3/2013 | Kim |
| 8,406,845 B2 | 3/2013 | Komistek et al. |
| 8,411,931 B2 | 4/2013 | Zhou |
| 8,427,538 B2 | 4/2013 | Ahiska |
| 8,428,319 B2 | 4/2013 | Tsin et al. |
| 8,571,293 B2 | 10/2013 | Ernst et al. |
| 8,615,127 B2 | 12/2013 | Fitzpatrick |
| 8,744,154 B2 | 6/2014 | Van Den Brink |
| 8,848,977 B2 | 9/2014 | Bammer et al. |
| 8,862,420 B2 | 10/2014 | Ferran et al. |
| 8,953,847 B2 | 2/2015 | Moden |
| 8,996,094 B2 | 3/2015 | Schouenborg et al. |
| 9,076,212 B2 | 7/2015 | Ernst et al. |
| 9,082,177 B2 | 7/2015 | Sebok |
| 9,084,629 B1 | 7/2015 | Rosa |
| 9,103,897 B2 | 8/2015 | Herbst et al. |
| 9,138,175 B2 | 9/2015 | Ernst et al. |
| 9,173,715 B2 | 11/2015 | Baumgartner |
| 9,176,932 B2 | 11/2015 | Baggen et al. |
| 9,194,929 B2 | 11/2015 | Siegert et al. |
| 9,305,365 B2 | 4/2016 | Lovberg et al. |
| 9,318,012 B2 * | 4/2016 | Johnson ............. G08B 21/0476 |
| 9,395,386 B2 | 7/2016 | Corder et al. |
| 9,451,926 B2 | 9/2016 | Kinahan et al. |
| 9,629,595 B2 * | 4/2017 | Walker .................. A61B 5/062 |
| 2002/0082496 A1 | 6/2002 | Kuth |
| 2002/0091422 A1 | 7/2002 | Greenberg et al. |
| 2002/0115931 A1 | 8/2002 | Strauss et al. |
| 2002/0180436 A1 | 12/2002 | Dale et al. |
| 2002/0188194 A1 | 12/2002 | Cosman |
| 2003/0063292 A1 | 4/2003 | Mostafavi |
| 2003/0088177 A1 | 5/2003 | Totterman et al. |
| 2003/0116166 A1 | 6/2003 | Anthony |
| 2003/0130574 A1 | 7/2003 | Stoyle |
| 2004/0071324 A1 | 4/2004 | Norris et al. |
| 2004/0116804 A1 | 6/2004 | Mostafavi |
| 2004/0140804 A1 | 7/2004 | Polzin et al. |
| 2004/0171927 A1 | 9/2004 | Lowen et al. |
| 2005/0027194 A1 | 2/2005 | Adler et al. |
| 2005/0054910 A1 | 3/2005 | Tremblay et al. |
| 2005/0105772 A1 | 5/2005 | Voronka et al. |
| 2005/0107685 A1 | 5/2005 | Seeber |
| 2005/0137475 A1 | 6/2005 | Dold et al. |
| 2005/0148854 A1 | 7/2005 | Ito et al. |
| 2005/0283068 A1 | 12/2005 | Zuccoloto et al. |
| 2006/0004281 A1 | 1/2006 | Saracen |
| 2006/0045310 A1 | 3/2006 | Tu et al. |
| 2006/0074292 A1 | 4/2006 | Thomson et al. |
| 2006/0241405 A1 | 10/2006 | Leitner et al. |
| 2007/0093709 A1 | 4/2007 | Abernathie |
| 2007/0206836 A1 | 9/2007 | Yoon |
| 2007/0239169 A1 | 10/2007 | Plaskos et al. |
| 2007/0280508 A1 | 12/2007 | Ernst et al. |
| 2008/0039713 A1 | 2/2008 | Thomson et al. |
| 2008/0181358 A1 | 7/2008 | Van Kampen et al. |
| 2008/0183074 A1 | 7/2008 | Carls et al. |
| 2008/0212835 A1 | 9/2008 | Tavor |
| 2008/0221442 A1 | 9/2008 | Tolowsky et al. |
| 2008/0273754 A1 | 11/2008 | Hick et al. |
| 2008/0287728 A1 | 11/2008 | Mostafavi |
| 2008/0287780 A1 | 11/2008 | Chase et al. |
| 2008/0317313 A1 | 12/2008 | Goddard et al. |
| 2009/0028411 A1 | 1/2009 | Pfeuffer |
| 2009/0052760 A1 | 2/2009 | Smith et al. |
| 2009/0185663 A1 | 7/2009 | Gaines, Jr. et al. |
| 2009/0209846 A1 | 8/2009 | Bammer |
| 2009/0253985 A1 | 10/2009 | Shachar et al. |
| 2009/0304297 A1 | 12/2009 | Adabala et al. |
| 2009/0306499 A1 | 12/2009 | Van Vorhis et al. |
| 2010/0054579 A1 | 3/2010 | Okutomi |
| 2010/0057059 A1 | 3/2010 | Makino |
| 2010/0059679 A1 | 3/2010 | Albrecht |
| 2010/0069742 A1 | 3/2010 | Partain et al. |
| 2010/0091089 A1 | 4/2010 | Cromwell et al. |
| 2010/0099981 A1 | 4/2010 | Fishel |
| 2010/0125191 A1 | 5/2010 | Sahin |
| 2010/0137709 A1 | 6/2010 | Gardner et al. |
| 2010/0148774 A1 | 6/2010 | Kamata |
| 2010/0149099 A1 | 6/2010 | Elias |
| 2010/0149315 A1 | 6/2010 | Qu |
| 2010/0160775 A1 | 6/2010 | Pankratov |
| 2010/0164862 A1 | 7/2010 | Sullivan |
| 2010/0165293 A1 | 7/2010 | Tanassi et al. |
| 2010/0167246 A1 | 7/2010 | Ghajar |
| 2010/0172567 A1 | 7/2010 | Prokoski |
| 2010/0177929 A1 | 7/2010 | Kurtz |
| 2010/0178966 A1 | 7/2010 | Seydoux |
| 2010/0179390 A1 | 7/2010 | Davis |
| 2010/0179413 A1 | 7/2010 | Kadour et al. |
| 2010/0183196 A1 | 7/2010 | Fu et al. |
| 2010/0191631 A1 | 7/2010 | Weidmann |
| 2010/0194879 A1 | 8/2010 | Pasveer |
| 2010/0198067 A1 | 8/2010 | Mahfouz |
| 2010/0198101 A1 | 8/2010 | Song |
| 2010/0198112 A1 | 8/2010 | Maad |
| 2010/0199232 A1 | 8/2010 | Mistry |
| 2010/0210350 A9 | 8/2010 | Walker |
| 2010/0214267 A1 | 8/2010 | Radivojevic |
| 2010/0231511 A1 | 9/2010 | Henty |
| 2010/0231692 A1 | 9/2010 | Perlman |
| 2010/0245536 A1 | 9/2010 | Huitema |
| 2010/0245593 A1 | 9/2010 | Kim |
| 2010/0251924 A1 | 10/2010 | Taylor |
| 2010/0253762 A1 | 10/2010 | Cheong |
| 2010/0268072 A1 | 10/2010 | Hall et al. |
| 2010/0277571 A1 | 11/2010 | Xu |
| 2010/0282902 A1 | 11/2010 | Rajasingham |
| 2010/0283833 A1 | 11/2010 | Yeh |
| 2010/0284119 A1 | 11/2010 | Coakley |
| 2010/0289899 A1 | 11/2010 | Hendron |
| 2010/0290668 A1 | 11/2010 | Friedman |
| 2010/0292841 A1 | 11/2010 | Wickham |
| 2010/0295718 A1 | 11/2010 | Mohamadi |
| 2010/0296701 A1 | 11/2010 | Hu |
| 2010/0302142 A1 | 12/2010 | French |
| 2010/0303289 A1 | 12/2010 | Polzin |
| 2010/0311512 A1 | 12/2010 | Lock |
| 2010/0321505 A1 | 12/2010 | Kokubun |
| 2010/0328055 A1 | 12/2010 | Fong |
| 2010/0328201 A1 | 12/2010 | Marvit |
| 2010/0328267 A1 | 12/2010 | Chen |
| 2010/0330912 A1 | 12/2010 | Saila |
| 2011/0001699 A1 | 1/2011 | Jacobsen |
| 2011/0006991 A1 | 1/2011 | Elias |
| 2011/0007939 A1 | 1/2011 | Teng |
| 2011/0007946 A1 | 1/2011 | Liang |
| 2011/0008759 A1 | 1/2011 | Usui |
| 2011/0015521 A1 | 1/2011 | Faul |
| 2011/0019001 A1 | 1/2011 | Rhoads |
| 2011/0025853 A1 | 2/2011 | Richardson |
| 2011/0038520 A1 | 2/2011 | Yui |
| 2011/0043631 A1 | 2/2011 | Marman |
| 2011/0043759 A1 | 2/2011 | Bushinsky |
| 2011/0050562 A1 | 3/2011 | Schoen |
| 2011/0050569 A1 | 3/2011 | Marvit |
| 2011/0050947 A1 | 3/2011 | Marman |
| 2011/0052002 A1 | 3/2011 | Cobb |
| 2011/0052003 A1 | 3/2011 | Cobb |
| 2011/0052015 A1 | 3/2011 | Saund |
| 2011/0054870 A1 | 3/2011 | Dariush |
| 2011/0057816 A1 | 3/2011 | Noble |
| 2011/0058020 A1 | 3/2011 | Dieckmann |
| 2011/0069207 A1 | 3/2011 | Steinberg |
| 2011/0074675 A1 | 3/2011 | Shiming |
| 2011/0081000 A1 | 4/2011 | Gertner |
| 2011/0081043 A1 | 4/2011 | Sabol |
| 2011/0085704 A1 | 4/2011 | Han |

(56) References Cited

U.S. PATENT DOCUMENTS

| | | |
|---|---|---|
| 2011/0092781 A1 | 4/2011 | Gertner |
| 2011/0102549 A1 | 5/2011 | Takahashi |
| 2011/0105883 A1 | 5/2011 | Lake et al. |
| 2011/0105893 A1 | 5/2011 | Akins et al. |
| 2011/0115793 A1 | 5/2011 | Grycewicz |
| 2011/0115892 A1 | 5/2011 | Fan |
| 2011/0116683 A1 | 5/2011 | Kramer et al. |
| 2011/0117528 A1 | 5/2011 | Marciello et al. |
| 2011/0118032 A1 | 5/2011 | Zalewski |
| 2011/0133917 A1 | 6/2011 | Zeng |
| 2011/0142411 A1 | 6/2011 | Camp |
| 2011/0150271 A1 | 6/2011 | Lee |
| 2011/0157168 A1 | 6/2011 | Bennett |
| 2011/0157358 A1 | 6/2011 | Bell |
| 2011/0157370 A1 | 6/2011 | Livesey |
| 2011/0160569 A1 | 6/2011 | Cohen et al. |
| 2011/0172060 A1 | 7/2011 | Morales |
| 2011/0172521 A1 | 7/2011 | Zdeblick et al. |
| 2011/0175801 A1 | 7/2011 | Markovic |
| 2011/0175809 A1 | 7/2011 | Markovic |
| 2011/0175810 A1 | 7/2011 | Markovic |
| 2011/0176723 A1 | 7/2011 | Ali et al. |
| 2011/0180695 A1 | 7/2011 | Li |
| 2011/0181893 A1 | 7/2011 | MacFarlane |
| 2011/0182472 A1 | 7/2011 | Hansen |
| 2011/0187640 A1 | 8/2011 | Jacobsen |
| 2011/0193939 A1 | 8/2011 | Vassigh |
| 2011/0199461 A1 | 8/2011 | Horio |
| 2011/0201916 A1 | 8/2011 | Duyn et al. |
| 2011/0201939 A1 | 8/2011 | Hubschman et al. |
| 2011/0202306 A1 | 8/2011 | Eng |
| 2011/0205358 A1 | 8/2011 | Aota |
| 2011/0207089 A1 | 8/2011 | Lagettie |
| 2011/0208437 A1 | 8/2011 | Teicher |
| 2011/0216002 A1 | 9/2011 | Weising |
| 2011/0216180 A1 | 9/2011 | Pasini |
| 2011/0221770 A1 | 9/2011 | Kruglick |
| 2011/0229862 A1 | 9/2011 | Parikh |
| 2011/0230755 A1 | 9/2011 | MacFarlane et al. |
| 2011/0234807 A1 | 9/2011 | Jones |
| 2011/0234834 A1 | 9/2011 | Sugimoto |
| 2011/0235855 A1 | 9/2011 | Smith |
| 2011/0237933 A1 | 9/2011 | Cohen |
| 2011/0242134 A1 | 10/2011 | Miller |
| 2011/0244939 A1 | 10/2011 | Cammegh |
| 2011/0250929 A1 | 10/2011 | Lin |
| 2011/0251478 A1 | 10/2011 | Wieczorek |
| 2011/0255845 A1 | 10/2011 | Kikuchi |
| 2011/0257566 A1 | 10/2011 | Burdea |
| 2011/0260965 A1 | 10/2011 | Kim |
| 2011/0262002 A1 | 10/2011 | Lee |
| 2011/0267427 A1 | 11/2011 | Goh |
| 2011/0267456 A1 | 11/2011 | Adermann |
| 2011/0275957 A1 | 11/2011 | Bhandari |
| 2011/0276396 A1 | 11/2011 | Rathod |
| 2011/0279663 A1 | 11/2011 | Fan |
| 2011/0285622 A1 | 11/2011 | Marti |
| 2011/0286010 A1 | 11/2011 | Kusik et al. |
| 2011/0291925 A1 | 12/2011 | Isarel |
| 2011/0293143 A1 | 12/2011 | Narayanan et al. |
| 2011/0293146 A1 | 12/2011 | Grycewicz |
| 2011/0298708 A1 | 12/2011 | Hsu |
| 2011/0298824 A1 | 12/2011 | Lee |
| 2011/0300994 A1 | 12/2011 | Verkaaik |
| 2011/0301449 A1 | 12/2011 | Maurer, Jr. |
| 2011/0301934 A1 | 12/2011 | Tardis |
| 2011/0303214 A1 | 12/2011 | Welle |
| 2011/0304541 A1 | 12/2011 | Dalal |
| 2011/0304650 A1 | 12/2011 | Canpillo |
| 2011/0304706 A1 | 12/2011 | Border |
| 2011/0306867 A1 | 12/2011 | Gopinathan |
| 2011/0310220 A1 | 12/2011 | McEldowney |
| 2011/0310226 A1 | 12/2011 | McEldowney |
| 2011/0316994 A1 | 12/2011 | Lemchen |
| 2011/0317877 A1 | 12/2011 | Bell |
| 2012/0002112 A1 | 1/2012 | Huang |
| 2012/0004791 A1 | 1/2012 | Buelthoff |
| 2012/0007839 A1 | 1/2012 | Tsao et al. |
| 2012/0019645 A1 | 1/2012 | Maltz |
| 2012/0020524 A1 | 1/2012 | Ishikawa |
| 2012/0021806 A1 | 1/2012 | Naltz |
| 2012/0027226 A1 | 2/2012 | Desenberg |
| 2012/0029345 A1 | 2/2012 | Mahfouz et al. |
| 2012/0032882 A1 | 2/2012 | Schlachta |
| 2012/0033083 A1 | 2/2012 | Horvinger |
| 2012/0035462 A1 | 2/2012 | Maurer, Jr. et al. |
| 2012/0039505 A1 | 2/2012 | Vastide |
| 2012/0044363 A1 | 2/2012 | Lu |
| 2012/0045091 A1 | 2/2012 | Kaganovich |
| 2012/0049453 A1 | 3/2012 | Morichau-Beauchant et al. |
| 2012/0051588 A1 | 3/2012 | McEldowney |
| 2012/0051664 A1 | 3/2012 | Gopalakrishnan et al. |
| 2012/0052949 A1 | 3/2012 | Weitzner |
| 2012/0056982 A1 | 3/2012 | Katz |
| 2012/0057640 A1 | 3/2012 | Shi |
| 2012/0065492 A1 | 3/2012 | Gertner et al. |
| 2012/0065494 A1 | 3/2012 | Gertner et al. |
| 2012/0072041 A1 | 3/2012 | Miller |
| 2012/0075166 A1 | 3/2012 | Marti |
| 2012/0075177 A1 | 3/2012 | Jacobsen |
| 2012/0076369 A1 | 3/2012 | Abramovich |
| 2012/0081504 A1 | 4/2012 | Ng |
| 2012/0083314 A1 | 4/2012 | Ng |
| 2012/0083960 A1 | 4/2012 | Zhu |
| 2012/0086778 A1 | 4/2012 | Lee |
| 2012/0086809 A1 | 4/2012 | Lee |
| 2012/0092445 A1 | 4/2012 | McDowell |
| 2012/0092502 A1 | 4/2012 | Knasel |
| 2012/0093481 A1 | 4/2012 | McDowell |
| 2012/0098938 A1 | 4/2012 | Jin |
| 2012/0101388 A1 | 4/2012 | Tripathi |
| 2012/0105573 A1 | 5/2012 | Apostolopoulos |
| 2012/0106814 A1 | 5/2012 | Gleason et al. |
| 2012/0108909 A1 | 5/2012 | Slobounov et al. |
| 2012/0113140 A1 | 5/2012 | Hilliges |
| 2012/0113223 A1 | 5/2012 | Hilliges |
| 2012/0116202 A1 | 5/2012 | Bangera |
| 2012/0119999 A1 | 5/2012 | Harris |
| 2012/0120072 A1 | 5/2012 | Se |
| 2012/0120237 A1 | 5/2012 | Trepess |
| 2012/0120243 A1 | 5/2012 | Chien |
| 2012/0120277 A1 | 5/2012 | Tsai |
| 2012/0121124 A1 | 5/2012 | Bammer |
| 2012/0124604 A1 | 5/2012 | Small |
| 2012/0127319 A1 | 5/2012 | Rao |
| 2012/0133616 A1 | 5/2012 | Nishihara |
| 2012/0133889 A1 | 5/2012 | Bergt |
| 2012/0143029 A1 | 6/2012 | Silverstein |
| 2012/0143212 A1 | 6/2012 | Madhani |
| 2012/0154272 A1 | 6/2012 | Hildreth |
| 2012/0154511 A1 | 6/2012 | Hsu |
| 2012/0154536 A1 | 6/2012 | Stoker |
| 2012/0154579 A1 | 6/2012 | Hampapur |
| 2012/0156661 A1 | 6/2012 | Smith |
| 2012/0158197 A1 | 6/2012 | Hinman |
| 2012/0162378 A1 | 6/2012 | El Dokor et al. |
| 2012/0165964 A1 | 6/2012 | Flaks |
| 2012/0167143 A1 | 6/2012 | Longet |
| 2012/0169841 A1 | 7/2012 | Chemali |
| 2012/0176314 A1 | 7/2012 | Jeon |
| 2012/0184371 A1 | 7/2012 | Shum |
| 2012/0188237 A1 | 7/2012 | Han |
| 2012/0188371 A1 | 7/2012 | Chen |
| 2012/0194422 A1 | 8/2012 | El Dokor |
| 2012/0194517 A1 | 8/2012 | Izadi et al. |
| 2012/0194561 A1 | 8/2012 | Grossinger |
| 2012/0195466 A1 | 8/2012 | Teng |
| 2012/0196660 A1 | 8/2012 | El Dokor et al. |
| 2012/0197135 A1 | 8/2012 | Slatkine |
| 2012/0200676 A1 | 8/2012 | Huitema |
| 2012/0201428 A1 | 8/2012 | Joshi et al. |
| 2012/0206604 A1 | 8/2012 | Jones |
| 2012/0212594 A1 | 8/2012 | Barnes |
| 2012/0218407 A1 | 8/2012 | Chien |

(56) References Cited

U.S. PATENT DOCUMENTS

| | | |
|---|---|---|
| 2012/0218421 A1 | 8/2012 | Chien |
| 2012/0220233 A1 | 8/2012 | Teague |
| 2012/0224666 A1 | 9/2012 | Speller |
| 2012/0224743 A1 | 9/2012 | Rodriguez |
| 2012/0225718 A1 | 9/2012 | Zhang |
| 2012/0229643 A1 | 9/2012 | Chidanand |
| 2012/0229651 A1 | 9/2012 | Takizawa |
| 2012/0230561 A1 | 9/2012 | Qureshi |
| 2012/0235896 A1 | 9/2012 | Jacobsen |
| 2012/0238337 A1 | 9/2012 | French |
| 2012/0242816 A1 | 9/2012 | Cruz |
| 2012/0249741 A1 | 10/2012 | Maciocci |
| 2012/0253201 A1 | 10/2012 | Reinhold |
| 2012/0253241 A1 | 10/2012 | Levital et al. |
| 2012/0262540 A1 | 10/2012 | Rondinelli |
| 2012/0262558 A1 | 10/2012 | Boger |
| 2012/0262583 A1 | 10/2012 | Bernal |
| 2012/0268124 A1 | 10/2012 | Herbst et al. |
| 2012/0275649 A1 | 11/2012 | Cobb |
| 2012/0276995 A1 | 11/2012 | Lansdale |
| 2012/0277001 A1 | 11/2012 | Lansdale |
| 2012/0281093 A1 | 11/2012 | Fong |
| 2012/0281873 A1 | 11/2012 | Brown |
| 2012/0288142 A1 | 11/2012 | Gossweiler, III |
| 2012/0288852 A1 | 11/2012 | Willson |
| 2012/0289334 A9 | 11/2012 | Mikhailov |
| 2012/0289822 A1 | 11/2012 | Shachar et al. |
| 2012/0293412 A1 | 11/2012 | El Dokor |
| 2012/0293506 A1 | 11/2012 | Vertucci |
| 2012/0293663 A1 | 11/2012 | Liu |
| 2012/0294511 A1 | 11/2012 | Datta |
| 2012/0300961 A1 | 11/2012 | Moeller |
| 2012/0303839 A1 | 11/2012 | Jackson |
| 2012/0304126 A1 | 11/2012 | Lavigne |
| 2012/0307075 A1 | 12/2012 | Margalit |
| 2012/0307207 A1 | 12/2012 | Abraham |
| 2012/0314066 A1 | 12/2012 | Lee |
| 2012/0315016 A1 | 12/2012 | Fung |
| 2012/0319946 A1 | 12/2012 | El Dokor |
| 2012/0319989 A1 | 12/2012 | Argiro |
| 2012/0320219 A1 | 12/2012 | David |
| 2012/0326966 A1 | 12/2012 | Rauber |
| 2012/0326976 A1 | 12/2012 | Markovic |
| 2012/0326979 A1 | 12/2012 | Geisert |
| 2012/0327241 A1 | 12/2012 | Howe |
| 2012/0327246 A1 | 12/2012 | Senior et al. |
| 2013/0002866 A1 | 1/2013 | Hampapur |
| 2013/0002879 A1 | 1/2013 | Weber |
| 2013/0002900 A1 | 1/2013 | Gossweiler, III |
| 2013/0009865 A1 | 1/2013 | Valik |
| 2013/0010071 A1 | 1/2013 | Valik |
| 2013/0013452 A1 | 1/2013 | Dennard |
| 2013/0016009 A1 | 1/2013 | Godfrey |
| 2013/0016876 A1 | 1/2013 | Wooley |
| 2013/0021434 A1 | 1/2013 | Ahiska |
| 2013/0021578 A1 | 1/2013 | Chen |
| 2013/0024819 A1 | 1/2013 | Rieffel |
| 2013/0030283 A1 | 1/2013 | Vortman et al. |
| 2013/0033640 A1 | 2/2013 | Lee |
| 2013/0033700 A1 | 2/2013 | Hallil |
| 2013/0035590 A1 | 2/2013 | Ma et al. |
| 2013/0035612 A1 | 2/2013 | Mason |
| 2013/0040720 A1 | 2/2013 | Cammegh |
| 2013/0041368 A1 | 2/2013 | Cunningham |
| 2013/0049756 A1 | 2/2013 | Ernst et al. |
| 2013/0057702 A1 | 3/2013 | Chavan |
| 2013/0064426 A1 | 3/2013 | Watkins, Jr. |
| 2013/0064427 A1 | 3/2013 | Picard |
| 2013/0065517 A1 | 3/2013 | Svensson |
| 2013/0066448 A1 | 3/2013 | Alonso |
| 2013/0066526 A1 | 3/2013 | Mondragon |
| 2013/0069773 A1 | 3/2013 | Li |
| 2013/0070201 A1 | 3/2013 | Shahidi |
| 2013/0070257 A1 | 3/2013 | Wong |
| 2013/0072787 A1 | 3/2013 | Wallace et al. |
| 2013/0076863 A1 | 3/2013 | Rappel |
| 2013/0076944 A1 | 3/2013 | Kosaka |
| 2013/0077823 A1 | 3/2013 | Mestha |
| 2013/0079033 A1 | 3/2013 | Gupta |
| 2013/0084980 A1 | 4/2013 | Hammontree |
| 2013/0088584 A1 | 4/2013 | Malhas |
| 2013/0093866 A1 | 4/2013 | Ohlhues et al. |
| 2013/0096439 A1 | 4/2013 | Lee |
| 2013/0102879 A1 | 4/2013 | MacLaren et al. |
| 2013/0102893 A1 | 4/2013 | Vollmer |
| 2013/0108979 A1 | 5/2013 | Daon |
| 2013/0113791 A1 | 5/2013 | Isaacs et al. |
| 2013/0211421 A1 | 8/2013 | Abovitz et al. |
| 2013/0281818 A1 | 10/2013 | Vija et al. |
| 2014/0073908 A1 | 3/2014 | Biber |
| 2014/0088410 A1 | 3/2014 | Wu |
| 2014/0148685 A1 | 5/2014 | Liu et al. |
| 2014/0159721 A1 | 6/2014 | Grodzki |
| 2014/0171784 A1 | 6/2014 | Ooi et al. |
| 2014/0378816 A1 | 12/2014 | Oh et al. |
| 2015/0085072 A1 | 3/2015 | Yan |
| 2015/0265220 A1 | 9/2015 | Ernst et al. |
| 2015/0297120 A1 | 10/2015 | Son et al. |
| 2015/0331078 A1 | 11/2015 | Speck et al. |
| 2015/0359464 A1 | 12/2015 | Oleson |
| 2015/0366527 A1 | 12/2015 | Yu et al. |
| 2016/0035108 A1 | 2/2016 | Yu et al. |
| 2016/0073962 A1 | 3/2016 | Yu et al. |
| 2016/0091592 A1 | 3/2016 | Beall et al. |
| 2016/0166205 A1 | 6/2016 | Ernst et al. |
| 2016/0189372 A1 | 6/2016 | Lovberg et al. |
| 2016/0228005 A1 | 8/2016 | Bammer et al. |
| 2016/0249984 A1 | 9/2016 | Janssen |
| 2016/0256713 A1 | 9/2016 | Saunders et al. |
| 2016/0262663 A1 | 9/2016 | MacLaren et al. |
| 2016/0287080 A1 | 10/2016 | Olesen et al. |
| 2016/0310229 A1 | 10/2016 | Bammer et al. |
| 2016/0313432 A1 | 10/2016 | Feiweier et al. |

FOREIGN PATENT DOCUMENTS

| | | |
|---|---|---|
| DE | 102004024470 | 12/2005 |
| EP | 0904733 | 3/1991 |
| EP | 1354564 | 10/2003 |
| EP | 1524626 | 4/2005 |
| EP | 2515139 | 10/2012 |
| EP | 2948056 | 12/2015 |
| EP | 2950714 | 12/2015 |
| JP | 03023838 | 5/1991 |
| WO | WO 96/17258 | 6/1996 |
| WO | WO 99/38449 | 8/1999 |
| WO | WO 00/72039 | 11/2000 |
| WO | WO 03/003796 | 1/2003 |
| WO | WO 2004/023783 | 3/2004 |
| WO | WO 2005/077293 | 8/2005 |
| WO | WO 2007/025301 | 3/2007 |
| WO | WO 2007/085241 A1 | 8/2007 |
| WO | WO 2007/136745 | 11/2007 |
| WO | WO 2009/101566 | 8/2009 |
| WO | WO 2009/129457 A1 | 10/2009 |
| WO | WO 2011/047467 A1 | 4/2011 |
| WO | WO 2011/113441 A2 | 9/2011 |
| WO | WO 2012/046202 A1 | 4/2012 |
| WO | WO 2013/032933 A2 | 3/2013 |
| WO | WO 2014/005178 | 1/2014 |
| WO | WO 2014/116868 | 7/2014 |
| WO | WO 2014/120734 | 8/2014 |
| WO | WO 2015/042138 | 3/2015 |
| WO | WO 2015/092593 | 6/2015 |
| WO | WO 2015/148391 | 10/2015 |
| WO | WO 2016/014718 | 1/2016 |

OTHER PUBLICATIONS

Hoff et al., "Analysis of Head Pose Accuracy in Augmented Reality", IEEE Transactions on Visualization and Computer Graphics 6, No. 4 (Oct.-Dec. 2000): 319-334.

(56) References Cited

OTHER PUBLICATIONS

Katsuki, et al., "Design of an Artificial Mark to Determine 3D Pose by Monocular Vision", 2003 IEEE International Conference on Robotics and Automation (Cat. No. 03CH37422), Sep. 14-19, 2003, pp. 995-1000 vol. 1.

Kiebel et al., "MRI and PET coregistration—a cross validation of statistical parametric mapping and automated image registration", Neuroimage 5(4):271-279 (1997).

Lerner, "Motion correction in fmri images", Technion-Israel Institute of Technology, Faculty of Computer Science (Feb. 2006).

Speck, et al., "Prospective real-time slice-by-slice Motion Correction for fMRI in Freely Moving Subjects", Magnetic Resonance Materials in Physics, Biology and Medicine., 19(2), 55-61, published May 9, 2006.

Yeo, et al. Motion correction in fMRI by mapping slice-to-volume with concurrent field-inhomogeneity correction:, International Conference on Medical Image Computing and Computer-Assisted Intervention, pp. 752-760 (2004).

US 7,906,604 Oct. 5, 2010, Bazakos (withdrawn).

Aksoy et al., "Hybrind Prospective and Retrospective Head Motion Correction to Mitigate Cross-Calibration Errors", NIH Publication, Nov. 2012.

Aksoy et al., "Real-Time Optical Motion Correction for Diffusion Tensor Imaging, Magnetic Resonance in Medicine" (Mar. 22, 2011) 66 366-378.

Andrews et al., "Prospective Motion Correction for Magnetic Resonance Spectroscopy Using Single Camera Retro-Grate Reflector Optical Tracking, Journal of Magnetic Resonance Imaging" (Feb. 2011) 33(2): 498-504.

Angeles et al., "The Online Solution of the Hand-Eye Problem", IEEE Transactions on Robotics and Automation, 16(6): 720-731 (Dec. 2000).

Anishenko et al., "A Motion Correction System for Brain Tomography Based on Biologically Motivated Models." 7th IEEE International Conference on Cybernetic Intelligent Systems, dated Sep. 9, 2008, in 9 pages.

Armstrong et al., "RGR-3D: Simple, cheap detection of 6-DOF pose for tele-operation, and robot programming and calibration", In Proc. 2002 Int. Conf. on Robotics and Automation, IEEE, Washington (May 2002).

Bandettini, Peter A., et al., "Processing Strategies for Time-Course Data Sets in Functional MRI of the Human Breain", Magnetic Resonance in Medicine 30: 161-173 (1993).

Barmet et al, Spatiotemporal Magnetic Field Monitoring for MR, Magnetic Resonance in Medicine (Feb. 1, 2008) 60: 187-197.

Bartels, LW, et al., "Endovascular interventional magnetic resonance imaging", Physics in Medicine and Biology 48: R37-R64 (2003).

Carranza-Herrezuelo et al, "Motion estimation of tagged cardiac magnetic resonance images using variational techniques" Elsevier, Computerized Medical Imaging and Graphics 34 (2010), pp. 514-522.

Chou, Jack C. K., et al., "Finding the Position and Orientation of a Sensor on a Robot Manipulator Using Quaternions", The International Journal of Robotics Research, 10(3): 240-254 (Jun. 1991).

Cofaru et al "Improved Newton-Raphson digital image correlation method for full-field displacement and strain calculation," Department of Materials Science and Engineering, Ghent University St-Pietersnieuwstraat, Nov. 20, 2010.

Ernst et al., "A Novel Phase and Frequency Navigator for Proton Magnetic Resonance Spectroscopy Using Water-Suppression Cycling, Magnetic Resonance in Medicine" (Jan. 2011) 65(1): 13-7.

Eviatar et al., "Real time head motion correction for functional MRI", In: Proceedings of the International Society for Magnetic Resonance in Medicine (1999) 269.

Forbes, Kristen P. N., et al., "Propeller MRI: Clinical Testing of a Novel Technique for Quantification and Compensation of Head Motion", Journal of Magnetic Resonance Imaging 14: 215-222 (2001).

Fulton et al., "Correction for Head Movements in Positron Emission Tomography Using an Optical Motion-Tracking System", IEEE Transactions on Nuclear Science, vol. 49(1):116-123 (Feb. 2002).

Glover, Gary H., et al., "Self-Navigated Spiral fMRI: Interleaved versus Single-shot", Magnetic Resonance in Medicine 39: 361-368 (1998).

Gumus et al., "Elimination of DWI signal dropouts using blipped gradients for dynamic restoration of gradient moment", ISMRM 20th Annual Meeting & Exhibition, May 7, 2012.

Herbst et al., "Preventing Signal Dropouts in DWI Using Continous Prospective Motion Correction", Proc. Intl. Soc. Mag. Reson. Med. 19 (May 2011) 170.

Herbst et al., "Prospective Motion Correction With Continuous Gradient Updates in Diffusion Weighted Imaging, Magnetic Resonance in Medicine" (2012) 67:326-338.

Horn, Berthold K. P., "Closed-form solution of absolute orientation using unit quaternions", Journal of the Optical Society of America, vol. 4, p. 629-642 (Apr. 1987).

International Preliminary Report on Patentability for Application No. PCT/US2015/022041, dated Oct. 6, 2016, in 8 pages.

International Preliminary Report on Patentability for Application No. PCT/US2007/011899, dated Jun. 8, 2008, in 13 pages.

International Search Report and Written Opinion for Application No. PCT/US2007/011899, dated Nov. 14, 2007.

International Search Report and Written Opinion for Application No. PCT/US2014/012806, dated May 15, 2014, in 15 pages.

International Search Report and Written Opinion for Application No. PCT/US2015/041615, dated Oct. 29, 2015, in 13 pages.

International Preliminary Report on Patentability for Application No. PCT/US2014/013546, dated Aug. 4, 2015, in 9 pages.

International Search Report and Written Opinion for Application No. PCT/US2015/022041, dated Jun. 29, 2015, in 9 pages.

Josefsson et al. "A flexible high-precision video system for digital recording of motor acts through lightweight reflect markers", Computer Methods and Programs in Biomedicine, vol. 49:111-129 (1996).

Kiruluta et al., "Predictive Head Movement Tracking Using a Kalman Filter", IEEE Trans. on Systems, Man, and Cybernetics—Part B: Cybernetics, 27(2):326-331 (Apr. 1997).

Maclaren et al., "Combined Prospective and Retrospective Motion Correction to Relax Navigator Requirements", Magnetic Resonance in Medicine (Feb. 11, 2011) 65:1724-1732.

MacLaren et al., "Navigator Accuracy Requirements for Prospective Motion Correction", Magnetic Resonance in Medicine (Jan. 2010) 63(1): 162-70.

MacLaren, "Prospective Motion Correction in MRI Using Optical Tracking Tape", Book of Abstracts, ESMRMB (2009).

Maclaren et al., "Measurement and correction of microscopic head motion during magnetic resonance imaging of the brain", PLOS ONE, vol. 7(11):1-9 (2012).

McVeigh et al., "Real-time, Interactive MRI for Cardiovascular Interventions", Academic Radiology, 12(9): 1121-1127 (2005).

Nehrke et al., "Prospective Correction of Affine Motion for Arbitrary MR Sequences on a Clinical Scanner", Magnetic Resonance in Medicine (Jun. 28, 2005) 54:1130-1138.

Norris et al., "Online motion correction for diffusion-weighted imaging using navigator echoes: application to RARE imaging without sensitivity loss", Magnetic Resonance in Medicine, vol. 45:729-733 (2001).

Ooi et al., "Prospective Real-Time Correction for Arbitrary Head Motion Using Active Markers", Magnetic Resonance in Medicine (Apr. 15, 2009) 62(4): 943-54.

Orchard et al., "MRI Reconstruction using real-time motion tracking: A simulation study", Signals, Systems and Computers, 42nd Annual Conference IEEE, Piscataway, NJ, USA (Oct. 26, 2008).

Park, Frank C. and Martin, Bryan J., "Robot Sensor Calibration: Solving AX-XB on the Euclidean Group", IEEE Transaction on Robotics and Automation, 10(5): 717-721 (Oct. 1994).

(56) References Cited

OTHER PUBLICATIONS

PCT Search Report from the International Searching Authority, dated Feb. 28, 2013, in 16 pages, regarding International Application No. PCT/US2012/052349.

Qin et al., "Prospective Head-Movement Correction for High-Resolution MRI Using an In-Bore Optical Tracking System", Magnetic Resonance in Medicine (Apr. 13, 2009) 62: 924-934.

Schulz et al., "First Embedded In-Bore System for Fast Optical Prospective Head Motion-Correction in MRI", Proceedings of the 28th Annual Scientific Meeting of the ESMRMB (Oct. 8, 2011) 369.

Shiu et al., "Calibration of Wrist-Mounted Robotic Sensors by Solving Homogeneous Transform Equations of the Form AX=XB", IEEE Transactions on Robotics and Automation, 5(1): 16-29 (Feb. 1989).

Tremblay et al., "Retrospective Coregistration of Functional Magnetic Resonance Imaging Data using External monitoring", Magnetic Resonance in Medicine 53:141-149 (2005).

Tsai et al., "A New Technique for Fully Autonomous and Efficient 3D Robotics Hand/Eye Calibration", IEEE Transaction on Robotics and Automation, 5(3): 345-358 (Jun. 1989).

Wang, Ching-Cheng, "Extrinsic Calibration of a Vision Sensor Mounted on a Robot", IEEE Transactions on Robotics and Automation, 8(2):161-175 (Apr. 1992).

Ward et al., "Prospective Multiaxial Motion Correction for fMRI", Magnetic Resonance in Medicine 43:459-469 (2000).

Welch at al., "Spherical Navigator Echoes for Full 3D Rigid Body Motion Measurement in MRI", Magnetic Resonance in Medicine 47:32-41 (2002).

Zaitsev, M., et al., "Prospective Real-Time Slice-by-Slice 3D Motion Correction for EPI Using an External Optical Motion Tracking System", Proc.Intl.Soc.Mag.Reson.Med.11:517(2004).

Zeitsev et al., "Magnetic resonance imaging of freely moving objects: Prospective real-time motion correction using an external optical motion tracking system", NeuroImage 31 (Jan. 29, 2006) 1038-1050.

\* cited by examiner

SYSTEMS, DEVICES, AND METHODS FOR DETECTING FALSE MOVEMENTS FOR MOTION CORRECTION DURING A MEDICAL IMAGING SCAN

CROSS-REFERENCE TO RELATED APPLICATIONS

The present application claims the benefit under 35 U.S.C. § 119(c) of U.S. Provisional Application No. 62/198,079, filed Jul. 28, 2015, and entitled "DETECTION OF FALSE MOVEMENTS FOR PROSPECTIVE MOTION CORRECTION FOR BIOMEDICAL IMAGING." The foregoing application is hereby incorporated herein by reference in its entirety under 37 C.F.R. § 1.57.

STATEMENT REGARDING FEDERALLY SPONSORED R&D

This invention was made with government support under grant number R01DA021146-01A1 awarded by the National Institutes of Health. The government has certain rights in the invention.

BACKGROUND

The disclosure relates generally to the field of motion tracking, and more specifically to systems, devices, and methods for detecting false movements for motion correction during a medical imaging scan.

There are various modalities for performing medical imaging of patients. For example, magnetic resonance imaging (MRI) is a medical imaging technique used in radiology to visualize internal structures of the body in detail. An MRI scanner is a device in which the patient or a portion of the patient's body is positioned within a powerful magnet where a magnetic field is used to align the magnetization of some atomic nuclei (usually hydrogen nuclei—protons) and radio frequency magnetic fields are applied to systematically alter the alignment of this magnetization. This causes the nuclei to produce a rotating magnetic field detectable by the scanner and this information is recorded to construct an image of the scanned region of the body. These scans typically take several minutes (up to about one hour in some instances), and in prior art devices any movement can degrade or ruin the images and require the scan to be repeated. For example, a scanner can be any medical or biomedical imaging system, such as MRI, CAT, PET, SPECT, nuclear medicine or the like.

Additionally, there are various radiation therapies, proton therapies, and other therapies that can be applied to patients. For example, radiation therapy can be applied to a targeted tissue region. In some systems, radiation therapy can be dynamically applied in response to patient movements. However, in many such systems, the tracking of patient movements does not have a high degree of accuracy. Accordingly, the use of such systems can result in the application of radiation therapy to non-targeted tissue regions, thereby unintentionally harming healthy tissue while intentionally affecting diseased tissue. The foregoing is also true for proton therapies and other therapies.

In order to track motion of patient movements during a medical imaging and/or therapeutic procedure, some modalities utilize one or more markers. For example, in some motion tracking technologies related to medical imaging, one or more markers can be placed on one or more portions of a patient's body, which are then tracked by one or more detectors. However, not all movement of such markers truly reflects motion of the patient, or the organ or organs of interest. For example, a marker may slip on the skin, or skin may slip relative to the organ(s) of interest, resulting in unwanted motion signals, which can be referred to herein as "false movement" or "false motion," and incorrect motion correction.

SUMMARY

The disclosure herein provides systems, devices, and methods for detecting false movements for motion correction during a medical imaging scan, such as during a magnetic resonance imaging scan.

An accurate and reliable method of determining the dynamic position and orientation of a patient's head or other body portion during MRI scanning or therapeutic procedures is a requirement in any attempt to compensate for subject motion during such procedures. Toward this end, one or more markers may be placed on one or more portions of a subject's body, which are then detected by one or more motion detectors. Such markers can provide points of reference in detecting subject motion, thereby facilitating the motion detection process. However, in some instances, marker movement may not reflect true movement of the subject. For example, a marker may slip or a marker may move due to skin movement rather than rigid body movement. As such, it can be advantageous to detect such false movements in correcting motion of a subject for medical imaging and/or therapeutic procedures in order to correct for only true movements of the subject.

In some embodiments, a computer-implemented method for determining false motion tracked by a motion correction system during a medical imaging scan, comprises: obtaining tracking data, wherein the tracking data reflects motion of a subject of the medical imaging scan or a portion thereof; determining by a false motion discriminator a likelihood of the obtained tracking data reflecting false motion, wherein the false motion is not reflective of true motion of the subject of the medical imaging scan or the portion thereof; and generating by the false motion discriminator a confidence level of the determined likelihood of the obtained tracking data reflecting false motion, wherein the motion correction system is configured to adjust output based on the confidence level, wherein the false motion discriminator comprises a computer processor and an electronic storage medium. In certain embodiments, the likelihood of the obtained tracking data reflecting false motion is based on at least one of velocity, acceleration, center of rotation, and axis of rotation of the motion of the subject. In certain embodiments, the likelihood of the obtained tracking data reflecting false motion is based on machine learning.

In some embodiments, a false motion classifier system for determining false motion tracked by a motion correction system during a medical imaging scan comprises: a first false motion discriminator configured to determine a center of rotation of a detected motion and further determine a first confidence level based on the center of rotation of the detected motion, wherein the first confidence level is indicative of the detected motion being true or false; a second false motion discriminator configured to determine a velocity of the detected motion and further determine a second confidence level based on the velocity of the detected motion, wherein the second confidence level is indicative of the detected motion being true or false; and a combination module configured to combine the first and second confidence levels to generate an output indicative of the detected motion being true or false, wherein an output indicative of the detected motion being false causes the motion correction system not to apply one or more motion correction processes to the detected motion.

In certain embodiments, the false motion classifier system further comprises a third false motion discriminator configured to determine a third confidence level indicative of the detected motion being true or false based on machine learning. In certain embodiments, the false motion classifier system further comprises a differential motion discriminator configured to determine a third confidence level indicative of the detected motion being true or false based on relative motion of two or more motion trackers used by the motion correction system. In certain embodiments, the false motion classifier system further comprises one or more external discriminators configured to determine one or more external confidence levels indicative of the detected motion being true or false. In certain embodiments, the one or more external discriminators are configured to determine the one or more external confidence levels based on at least one or more of noise and video tracking. In certain embodiments, the output is binary.

In some embodiments, a motion correction system for detecting and correcting motion by a subject during a medical imaging scan comprises: one or more markers placed on one or more portions of the subject; one or more detectors configured to track motion of the one or more markers; and a tracking quality classifier for determining false motion of the one or more markers, wherein the tracking quality classifier system comprises one or more false motion discriminators, wherein determination by the tracking quality classifier that a false motion of the one or more markers occurred causes the motion correction system not to apply one or more motion correction processes to the false motion.

In certain embodiments, the one or more false motion discriminators are configured to determine false motion of the one or more markers based on at least one or more of velocity, rotational center, and machine learning. In certain embodiments, the tracking quality classifier further comprises one or more external discriminators. In certain embodiments, the motion correction system further comprises a scanner control module configured to control a scanner for the medical imaging scan not to utilize acquired data during the false motion. In certain embodiments, the motion correction system further comprises a scanner control module configured to control a scanner for the medical imaging scan to repeat acquisitions of data initially acquired during the false motion.

For purposes of summarizing the invention and the advantages achieved over the prior art, certain objects and advantages are described herein. Of course, it is to be understood that not necessarily all such objects or advantages need to be achieved in accordance with any particular embodiment. Thus, for example, those skilled in the art will recognize that the invention may be embodied or carried out in a manner that can achieve or optimize one advantage or a group of advantages without necessarily achieving other objects or advantages.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

The foregoing and other features, aspects, and advantages of the present inventions are described in detail below with reference to the drawings of various embodiments, which are intended to illustrate and not to limit the inventions. The drawings comprise the following figures in which.

DETAILED DESCRIPTION

Figure 1A:
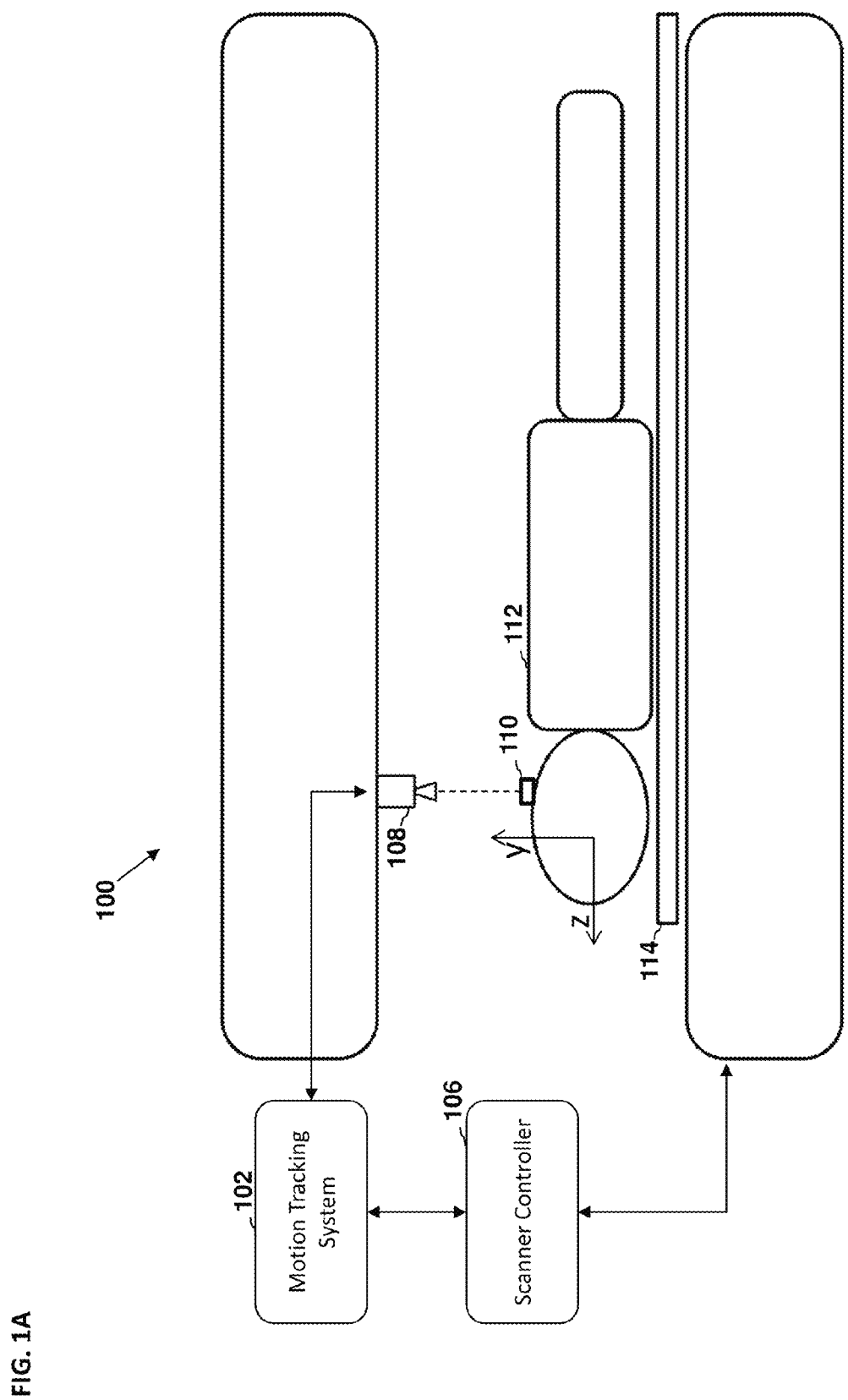
FIG. 1A illustrates an embodiment of a schematic diagram depicting a side view of a medical imaging scanner as a part of a motion compensation system.

Although several embodiments, examples, and illustrations are disclosed below, it will be understood by those of ordinary skill in the art that the inventions described herein extend beyond the specifically disclosed embodiments, examples, and illustrations and includes other uses of the inventions and obvious modifications and equivalents thereof. Embodiments of the inventions are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

With the use of diagnostic technologies and therapeutic technologies, it can be advantageous to track patient movement with a high degree of accuracy. Such high accuracy tracking can improve the imaging quality obtained and produced by diagnostic equipment, such as imaging technologies. Further, the use of high accuracy patient movement tracking technology can improve the application of patient therapies, such as radiation treatment, proton treatment, and the like. By accounting for patient movement with a high degree of accuracy, therapeutic technologies can apply therapies only to the targeted tissue and avoid healthy surrounding tissue. One of such methods to address motion during a medical imaging scan or therapeutic procedure is prospective motion correction, which involves tracking of the object of interest, such as the head or brain of a subject, and adjusting scan planes in real-time or near real-time such that they follow the movement, resulting in images without motion artifacts.

When an external tracking system is used, such as a camera-based system, the tracking system usually tracks the position of a marker that is assumed to reflect the position of the object to be imaged, such as the brain. For example, many existing technologies relating to motion detection and/or correction in the field of medical imaging and/or therapeutic procedures utilize one or more markers. One or more markers can be attached or placed on one or more different portions of a subject's body that is subject to the medical imaging or therapeutic procedure. Such markers can be detected by the motion detection and/or correction system. As such, prospective motion correction can generally involve (1) continuously tracking the motion of the object of interest with a sensor device, commonly using a marker attached to the object of interest, (2) sending tracking information from the sensor to the imaging device, and (3) continuously adjusting scan parameters of the imaging device in real-time or near real-time such that the image acquisition is locked relative to the mobile object of interest. The results can be images that show no, or reduced, motion artifacts compared to a scan that does not use prospective motion correction.

However, some problems may arise with the use of such markers. It is possible that such markers transiently do not reflect true subject movement. For instance, prospective motion correction relies on the assumption that the tracking marker accurately represents the motion of the object of interest. However, the actual tissue of interest can be situated inside the subject, whereas the marker can be attached to the surface or skin of the subject. As such, while the motion of a marker attached to the forehead skin would normally be assumed to reflect movement of the brain inside the skull, the skin and thus the marker may slip relative to the brain, for example when a subject is squinting or twitching. In such circumstances, the marker may fail to accurately reproduce motion of the tissue of interest and result in false marker movements. This can result in false correction signals and image artifacts. Such false marker movements can greatly reduce the robustness of prospective motion correction when applied to uncooperative subjects, and in the worst-case scenario can render otherwise high-quality images unusable.

As such, although the markers have moved thereby triggering the motion correction process, it may be advantageous to ignore such movements of the markers. Such movements of markers that ideally should not be accounted for by the system in the motion correction process can be called "false movements" or "false motions." In contrast, movements or motions of the markers that indeed should be accounted for in the motion correction process can be called "true motions" or "true movements."

The systems, methods, and devices described herein generally relate to achieving accurate and robust motion correction by detecting and accounting for such false movements. In other words, in some embodiments of the systems, methods, and devices described herein can be configured to detect false movements for motion correction during a medical imaging scan and/or therapeutic procedure, and thereby ensure that such false marker movements are not accounted for in the motion correction process. In certain embodiments, the systems, methods, and devices described herein detect the presence of or a high likelihood of such false marker movements. Upon detection of false movements, the imaging or therapeutic apparatus can be configured to transiently suppress acquisitions and subsequently repeat acquisitions or reconstruct images with partially missing data.

In other words, some of the systems, devices, and methods described herein involve detecting biomechanically unlikely motions of a marker, which can suggest a high probability that false marker movements are present. Based on such detection, a medical or biomedical imaging device or therapeutic device can be informed of potentially false marker movement conditions and may take measures to avoid applying false corrections, for instance, by not updating positions or by suspending acquisition of imaging data until the false motion condition is no longer present.

In certain embodiments, the systems, devices, and methods described herein can be utilized to determine false movement or motion without use of markers. In some embodiments, the systems, devices, and methods described herein can be applied to tracking systems where the sensing device or devices are directly located on the object of interest, such as the skin of the subject. In certain embodiments, the systems, devices, and methods described herein can be configured to detect false marker movement or false movement for body organs other than the head and/or brain of a subject.

Figure 1B:
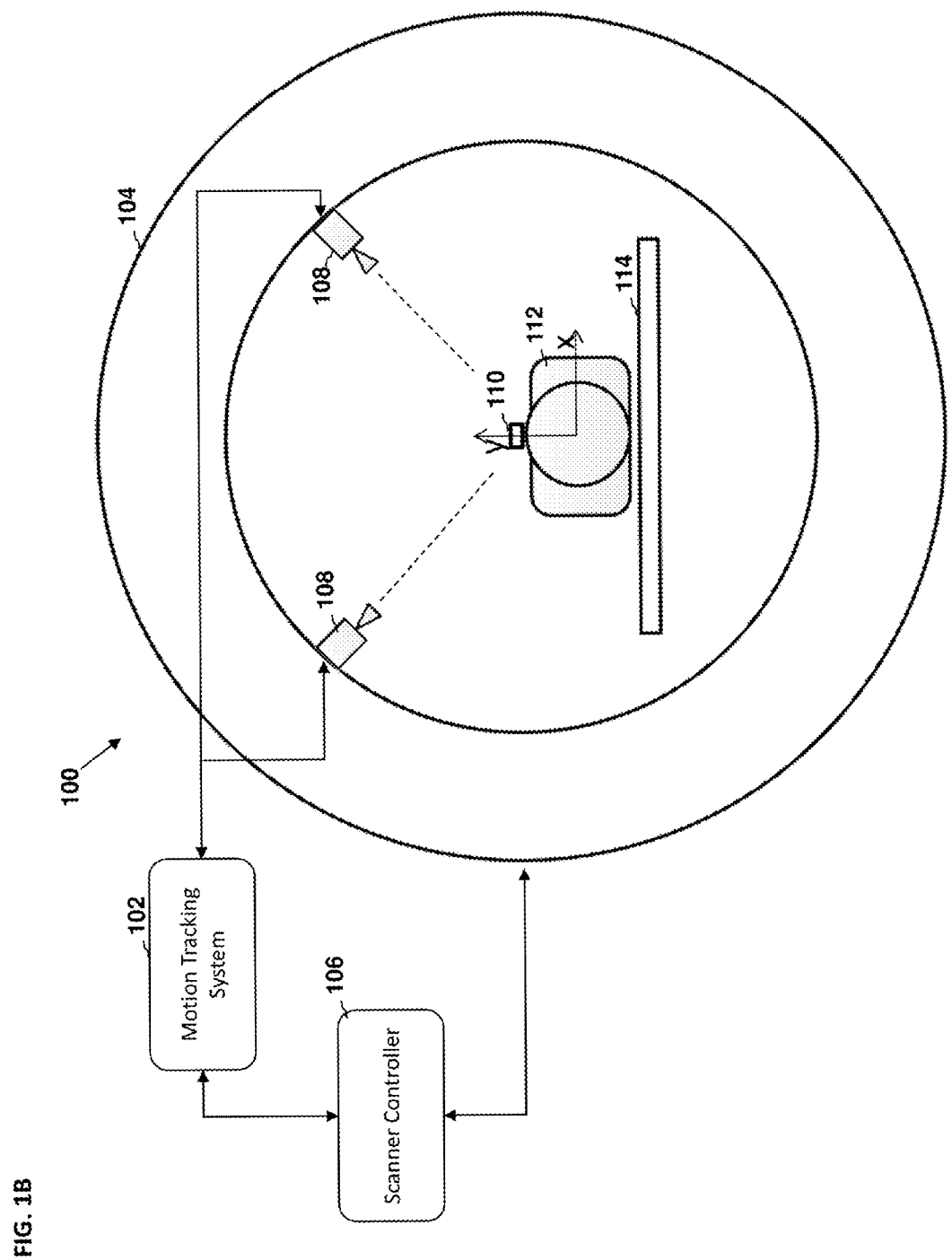
FIG. 1B illustrates an embodiment of a schematic diagram depicting a front view of a medical imaging scanner as a part of a motion compensation system.

Motion Compensation Systems and Medical Imaging Scanners or Therapeutic Procedures FIG. 1A is a schematic diagram illustrating a side view of a medical imaging scanner 104 as part of a motion compensation system 100 that is configured to determine false movements for motion correction. FIG. 1B is a schematic diagram illustrating a front view of a medical imaging scanner 104 as part of a motion compensation system 100 that is configured to detect and account for false movements for motion correction during a medical imaging scan or therapeutic procedure.

The motion compensation system 100 illustrated in FIGS. 1A and 1B can comprise a motion tracking system 102, a scanner, a scanner controller 106, one or more detectors 108, and one or more motion tracking markers or targets 110. In some embodiments, one or more markers 110 can be attached and/or otherwise placed on a subject 112. For example, the one or more markers 110 can be placed on the face of a subject 110 for imaging or therapeutic procedures directed to the head or brain of the subject. Similarly, the one or more markers 110 can be placed on other portions of a body of a subject 110 for imaging or therapeutic procedures directed to other portions of the body of the subject 110. The subject 110 can be positioned to lie on a table 114 of a medical imaging scanner 104. The scanner 104 can be, for example, a magnetic resonance imaging scanner or MRI scanner.

As depicted in FIGS. 1A and 1B, a three-dimensional coordinate system or space can be applied to a subject that is positioned inside a medical imaging scanner. For example, the center or substantially center of a particular portion of the subject 110 for observation can be thought of as having coordinates of (0, 0, 0). Further, a z-axis can be imposed along the longitudinal axis of the medical imaging scanner. In other words, the z-axis can be positioned along the length of the medical imaging scanner and along the height of a subject or patient that is positioned within the medical imaging scanner, thereby essentially coming out of the medical scanner. Similarly, an x-axis can be thought of as being positioned along the width of the medical imaging scanner or along the width of the patient or subject that is positioned within the medical imaging scanner. Furthermore, a y-axis can be thought of as extending along the height of the medical imaging scanner. For instance, the y-axis can be thought of as extending from the patient or subject located within the medical imaging scanner towards the one or more detectors 108.

Markers

Figure 2:
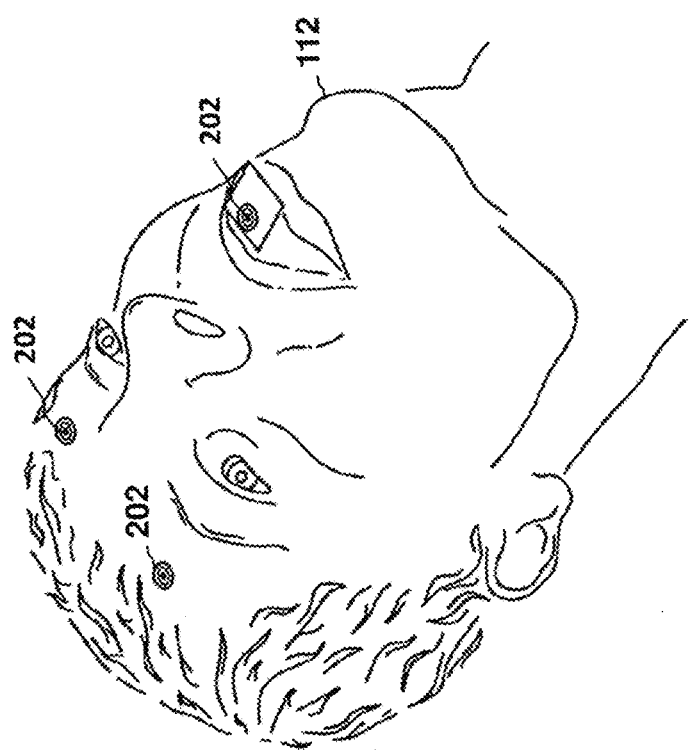
FIG. 2 illustrates a perspective view of an embodiment of one or more optical markers used for a motion compensation system.

As briefly discussed above, in many medical imaging scanning systems and/or therapeutic procedure systems that utilize motion detection and correction systems or methods, one or more markers can be utilized to track the position and movement or motion of the patient or subject. FIG. 2 illustrates an example of an embodiment where one or more markers are placed or attached to the face of a patient or subject for motion detection or correction purposes.

As depicted in FIG. 2, one or more markers 202 can be placed on the face or head of a patient or subject 112. In the example shown in FIG. 2, three of such markers 202 are placed on the patient or subject's head. For example, one or more markers 202 can be placed on the forehead of a subject or patient 112 and/or one or more markers 202 can be placed vis a vie a mouthpiece that is held by the mouth of a subject. In certain embodiments, one or more markers 202 can be placed on other portions of the subject as well. For example, one or more markers 202 can be placed on one or more sides of the subject's nose, nose bridge, cheek, cheekbone, eyes, eyelids, neck, chest, stomach, and/or any other portion of the body.

However, while such markers 202 can help the motion correction or detection system detect motion of the subject and correct for any unwanted movement by the subject, one or more of such markers 202 can also move unexpectedly and/or separately from a rigid body movement. For example, when one or more markers 202 are placed on the face of a subject or patient, any twitches on the skin of the patient, for example, if the patient sneezes, squints, frowns or makes any other facial expression, such markers 202 can move. However, if taking an MRI scan of a subject's brain, such false movements along the skin or surface of the patient only without any or substantial movement of the head or brain of the subject, ideally should not have any impact on the resulting scanned image. However if all such false movements or motions along the skin of a patient are accounted for by the motion correction system, the resulting scanned image may in fact be even more blurry compared to when no such motion correction was applied, because the brain or head of the subject did not actually move.

Tracking Quality Classifier—General

In some embodiments, the system can comprise one or more motion classifiers. For example, such motion classifiers can be configured to detect and/or classify a particular motion as being a false movement and/or true movement. Such motion classifier can be based on a physical model. In certain embodiments, the classifier may run in real-time, substantially real-time, or near real-time during a medical imaging process or therapeutic process and receive input from one or more motion tracking devices and/or systems.

In certain embodiments, tracking data obtained by the motion classifier can be sent to a false motion discriminator. A false motion discriminator can be configured to estimate a confidence level for false marker movement and forward the decision to the medical imaging or therapeutic device or system.

Figure 3:
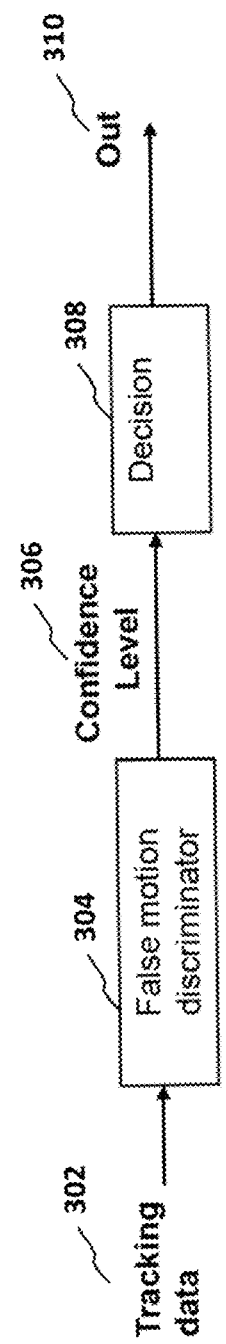
FIG. 3 is a block diagram depicting an embodiment of a simple tracking quality classifier.

FIG. 3 illustrates a block diagram depicting an embodiment of a simple tracking quality classifier. As depicted in FIG. 3, the system or motion classifier can be configured to track motion data of a subject in block 302. Such tracked motion data can be further analyzed by the system to detect whether the tracked motion is true or false. For example, in certain embodiments, the system can comprise a false motion discriminator at block 304 that is configured to determine whether the tracked motion is false or true motion. In certain embodiments, the system can comprise a plurality of false motion discriminators 304.

In some embodiments, the one or more false motion discriminators 304 can be configured to output one or more confidence levels 306 of the detected movement. For example, the system can be configured to output a confidence level that is high when the false motion discriminator determines that the detected movement or motion of the subject is highly likely to be false movement that should not be accounted for by the motion correction system. In contrast, the system can be configured to output a confidence level that is high when the false motion discriminator determines that the detected movement or motion of the subject is highly likely to be true movement that should be accounted for by the motion correction system. Similarly, in some embodiments, a low confidence level can correspond to a low likelihood of false movement or high likelihood of true movement. In certain embodiments, a low confidence level can correspond to a low likelihood of true movement or high likelihood of false movement.

In some embodiments, the confidence level that is determined by the one or more false motion discriminators 304 can be a unit-less number. For example, the confidence level can be on a scale of 0 to 1, 1 to 10, 1 to 100, and 1 to 1,000. In certain embodiments, the confidence level can be a percentage or ratio.

Based on the confidence level that is determined by the false motion discriminator 304, the system can be configured to output a decision 308 of the nature of the detected movement, which can then be utilized by the motion correction system of a medical imaging scanner or therapeutic procedure to either account for or not account for the tracked motion.

In some embodiments, the system comprises only one false motion discriminator. In other embodiments, the system can comprise a plurality of false motion discriminators. In certain embodiments, such false motion discriminators can be based on one or more parameters. For example, in some embodiments, a false motion discriminator 304 can be configured to determine the likelihood of a false motion or movement based on the velocity, acceleration, axis of rotation, central point of rotation, machine learning, and/or any combination of the above.

Velocity/Acceleration-Based Discriminator

In some embodiments, the system or one or false motion discriminators thereof can be configured to determine the likelihood of a false motion being present based on the velocity of movement or motion of one or more markers or trackers. For example, when a subject twitches or sneezes or the like movement of the marker can be substantially faster than when there is rigid body movement or physiological movement. Conditions associated with false marker movement, such as squinting, coughing or frowning are typically transient and involve velocities that are substantially higher than those for a typical physiologic motions, since the head has a high inertia compared to skin or marker. Accordingly, the velocity discriminator can be configured to provide a confidence level that the velocity of a given movement is outside of the physiologic range.

In certain embodiments, the system or one or false motion discriminators thereof can be configured to detect or otherwise receive the raw tracking data and further analyze such data by obtaining their first and/or second temporal derivatives of velocity and/or acceleration. Such velocities and/or acceleration may be used by a velocity-based discriminator to determine a likelihood of false movement. In certain embodiments, such obtained velocities and/or acceleration may be further sent to a set of discriminators, each of which can be configured to estimate confidence levels for conditions of false marker movement.

In some embodiments, if the velocity of a particular movement or motion of a marker at any given time is greater or equal to 10-20 mm/sec or 10-20°/sec, depending on whether the velocity is determined based on distance or angle of rotation, the system or velocity-based false motion discriminator can be configured to determine a high likelihood of false movement. Similarly, if the velocity of a particular movement or motion of a marker at any given time is lower or equal to 10-20 mm/sec or 10-20°/sec, the system or velocity-based false motion discriminator can be configured to determine a low likelihood of false movement or high likelihood of true movement.

In certain embodiments, the boundary for determining a high likelihood of false or true movement based on velocity of a particular marker can be about 1 mm/sec, about 2 mm/sec, about 3 mm/sec, about 4 mm/sec, about 5 mm/sec, about 6 mm/sec, about 7 mm/sec, about 8 mm/sec, about 9 mm/sec, about 10 mm/sec, about 11 mm/sec, about 12 mm/sec, about 13 mm/sec, about 14 mm/sec, about 15 mm/sec, about 16 mm/sec, about 17 mm/sec, about 18 mm/sec, about 19 mm/sec, about 20 mm/sec, about 21 mm/sec, about 22 mm/sec, about 23 mm/sec, about 24 mm/sec, about 25 mm/sec, about 26 mm/sec, about 27 mm/sec, about 28 mm/sec, about 29 mm/sec, about 30 mm/sec, about 1°/sec, about 2°/sec, about 3°/sec, about 4°/sec, about 5°/sec, about 6°/sec, about 7°/sec, about 8°/sec, about 9°/see, about 10°/sec, about 1°/sec, about 12°/sec, about 13°/sec, about 14°/sec, about 15°/sec, about 16°/sec, about 17°/sec, about 18°/sec, about 19°/sec, about 20°/sec, about 21°/sec, about 22°/sec, about 23°/sec, about 24°/sec, about 25°/sec, 26°/sec, 27°/sec, 28°/sec, 29°/sec, 30°/sec, and/or within a range defined by any two of the above-identified values.

Similarly, in some embodiments, the boundary for determining a high likelihood of false or true movement based on acceleration of a particular marker can be about 1 mm/sec$^2$, about 2 mm/sec$^2$, about 3 mm/sec$^2$, about 4 mm/sec$^2$, about 5 mm/sec$^2$, about 6 mm/sec$^2$, about 7 mm/sec$^2$, about 8 mm/sec, about 9 mm/sec$^2$, about 10 mm/sec$^2$, about 11 mm/sec$^2$, about 12 mm/sec$^2$, about 13 mm/sec$^2$, about 14 mm/sec$^2$, about 15 mm/sec$^2$, about 16 mm/sec$^2$, about 17 mm/sec$^2$, about 18 mm/sec$^2$, about 19 mm/sec$^2$, about 20 mm/sec$^2$, about 21 mm/sec$^2$, about 22 mm/sec$^2$, about 23 mm/sec$^2$, about 24 mm/sec$^2$, about 25 mm/sec$^2$, about 26 mm/sec$^2$, about 27 mm/sec$^2$, about 28 mm/sec$^2$, about 29 mm/sec$^2$, about 30 mm/sec$^2$, about 1°/sec$^2$, about 2°/sec$^2$, about 3°/sec$^2$, about 4°/sec$^2$, about 5°/sec$^2$, about 6°/sec$^2$, about 7°/sec$^2$, about 8°/sec$^2$, about 9°/sec$^2$, about 10°/sec$^2$, about 11°/sec$^2$, about 12°/sec$^2$, about 13°/sec$^2$, about 14°/sec$^2$, about 15°/sec$^2$, about 16°/sec$^2$, about 17°/sec$^2$, about 18°/sec$^2$, about 19°/sec$^2$, about 20°/sec$^2$, about 21°/sec$^2$, about 22°/sec$^2$, about 23°/sec$^2$, about 24°/sec$^2$, about 25°/sec$^2$, 26°/sec$^2$, 27°/sec$^2$, 280/sec$^2$, 29°/sec$^2$, 30°/sec$^2$, and/or within a range defined by any two of the above-identified values.

Center of Rotation-Based Discriminator

In some embodiments, the system or one or false motion discriminators thereof can be configured to determine the likelihood of a false motion being present based on the center of rotation of a movement or motion of one or more markers or trackers. In other words, in certain embodiments, a false motion discriminator can be configured to determine or estimate the likelihood of false movement or motion of a subject based on the anterior-posterior center (y) position of head rotations.

Physiological head movements commonly have a posterior rotational center. If the center or substantially center of a head of a patient or subject is assumed to be at a y=−0 position, physiological head movements commonly have a rotational center that is below 0 on the y axis. For example, the rotational center of a physiological head movement can be located along the y axis at around y=−50 mm, wherein y=0 is located at substantially the center of the subject's head. In contrast, a false marker motion or rotation can be thought of as being centered at an anterior attachment point. In a false marker motion, the rotational center can be assumed to be at a position along the y axis with a positive value. For example, the rotational center of a false marker motion can be at roughly y=80 mm. This is because most subjects inside a medical imaging scanner or therapeutic system are in a position with their head in contact with the bed of the scanner. As such, when the subject rotates his or her head the rotational center will usually be located near or at the center of the back of the subject's head that is contact with the bed of the scanner. In contrast, any movement along the skin or surface of the patient's head will tend to rotate along a rotational center that is located much higher than the back of the subject's head.

In other words, since brain MRI is generally performed with patients in a supine position, physiologic head rotations are typically centered where the back of the head is supported, which can be approximately 50 to 100 millimeters posterior of the MRI isocenter. Conversely, false marker movements typically involve skin motion at the marker attachment point, which can be at the forehead, nose, teeth, or any other position, and therefore a rotational center can be located 50 to 100 millimeters interior of the MRI isocenter. Based on such assumptions, in some embodiments, a false motion discriminator can be configured to utilize the tracking data from a single marker to estimate the anterior-posterior position of the axis of rotation. Accordingly, in certain embodiments, the false motion discriminator can be configured to provide a confidence level that a given rotation is centered close to the skin attachment point.

In some embodiments, the system or one or more false motion discriminators can be configured to detect or otherwise receive tracking data of one or more markers and determine the center of rotation of the movement. To determine the center of rotation, the system or one or more false motion discriminators can be configured to utilize one or more processes or methods. An embodiment of one of such methods is described below in connection with Appendix A below.

A-P Axis Rotation-Based Discriminator

In certain embodiments, a false motion discriminator can be configured to determine false motion based on the fact that human head movements in the tight space of an MRI radiofrequency (RF) coil are unlikely to involve major rotations about the anterior-posterior (A-P) axis, which can be thought of as connecting the nose to the back of the head of a subject. Additionally, if such rotations occur, they are generally centered at a point towards the neck. In other words, A-P rotations generally occur during motions dominated by left-right movements of the head or head shaking. Conversely, facial skin movements, such as squinting can result in relatively large and fast A-P rotations without proportionate left-right head movements. As such, in certain embodiments, the system or a false motion discriminator thereof can be configured to track and determine the rotation of a particular movement along the A-P axis and the scope thereof and/or determine left-right head movement in order to determine a likelihood of false of true motion. Consequently, a false motion discriminator based on A-P rotations can provide a confidence level that a given A-P rotation is outside of a biomechanically reasonable range in terms of velocity and not associated with a rotational center distant from the neck.

As such, in some embodiments, the system or a false motion discriminator thereof can be configured to determine the velocity of a particular movement or motion and also the rotational movement around the A-P axis using one or methods described herein. Based on such data, the system or false motion discriminator thereof can be further configured to determine whether the determined velocity, A-P rotation trend or movement, and/or both is within or outside of a biomechanically reasonable range for determining the likelihood of false or true movement.

Neural Network-Based Discriminator

In some embodiments, the system can comprise one or more false motion discriminators that involve sophisticated pattern recognition or machine learning approaches. For instance, in certain embodiments, a false motion discriminator can be configured to use an artificial neural network that is trained on tracking data from sample subjects who perform rigid head movements as well as non-rigid face movements or false movements, such as squinting, coughing, frowning or the like.

Figure 4:
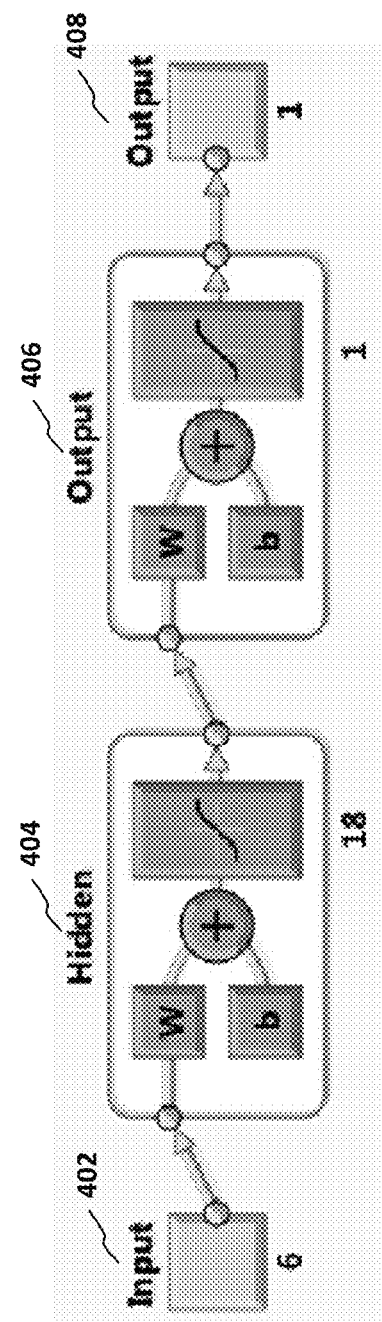
FIG. 4 is a block diagram depicting an embodiment of a neural network.

FIG. 4 is a block diagram depicting an embodiment of a neural network. As shown in FIG. 4, in certain embodiments, a false motion discriminator can comprise one or more probabilistic networks. Further, in some embodiments, the network can be a feed-forward neural network comprising a hidden layer 404 of 18 neurons and an output layer 406 of 1 neuron. In other embodiments, the hidden layer 404 and/or the output layer 406 can comprise any number of neurons.

A neural network can be trained to classify motion into rigid-body motion and skin-movement based on data collected from one or more volunteers or sample subjects who can perform both rigid and skin movement. For example, one or more markers can be attached to one or more portions of a volunteer, such as forehead, nose, etc., and a plurality of rigid and skin movement can be inputted into the system. In some embodiments, while the network can be trained using data from one marker, the presence of two markers can provide the network with the true information about the type of motion. In certain embodiments, the system can be binary, for example 0 can correspond to rigid-body motion and 1 can correspond to skin-movement.

Figure 5:
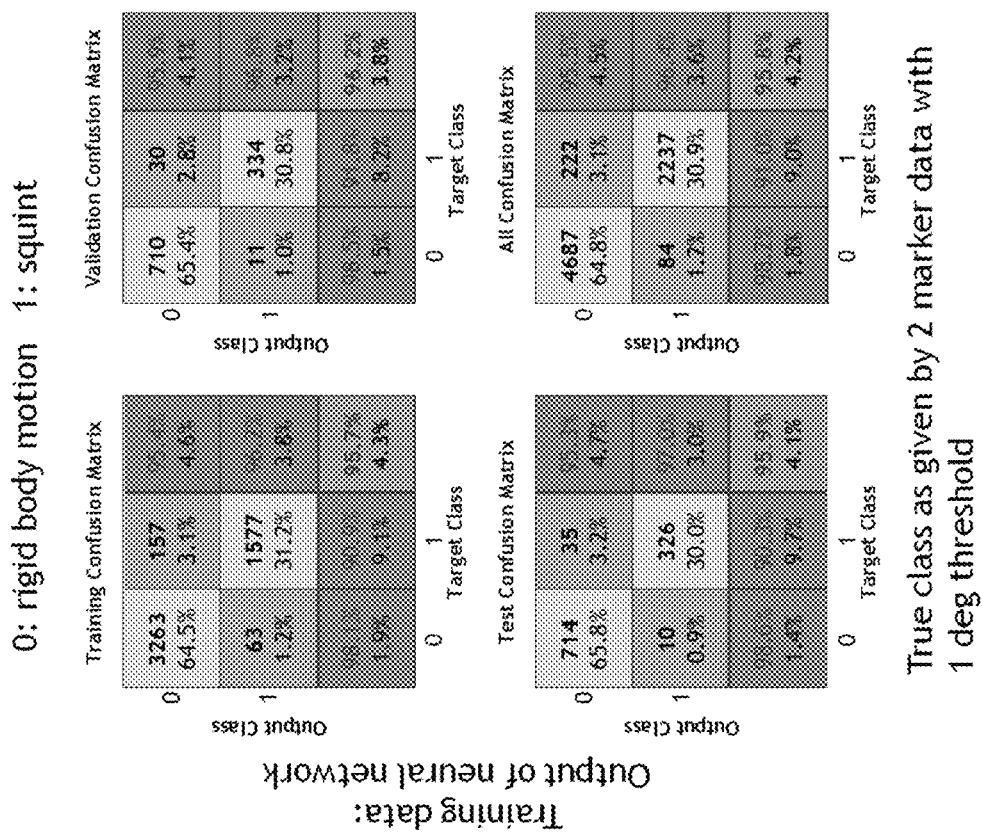
FIG. 5 is illustrates an example of an embodiment of various confusion matrices showing the results of training, validation, and testing of a neural network.

FIG. 5 illustrates an example of an embodiment of various confusion matrices showing the results of training, validation, and testing of a neural network.

Additionally, other well-established and/or non-neural discrimination methods can be utilized to detect conditions indicating false marker movements. For example, some embodiments may utilize a support vector machine for detecting conditions indicating false marker movements.

Complex Tracking Quality Classifier

Figure 6:
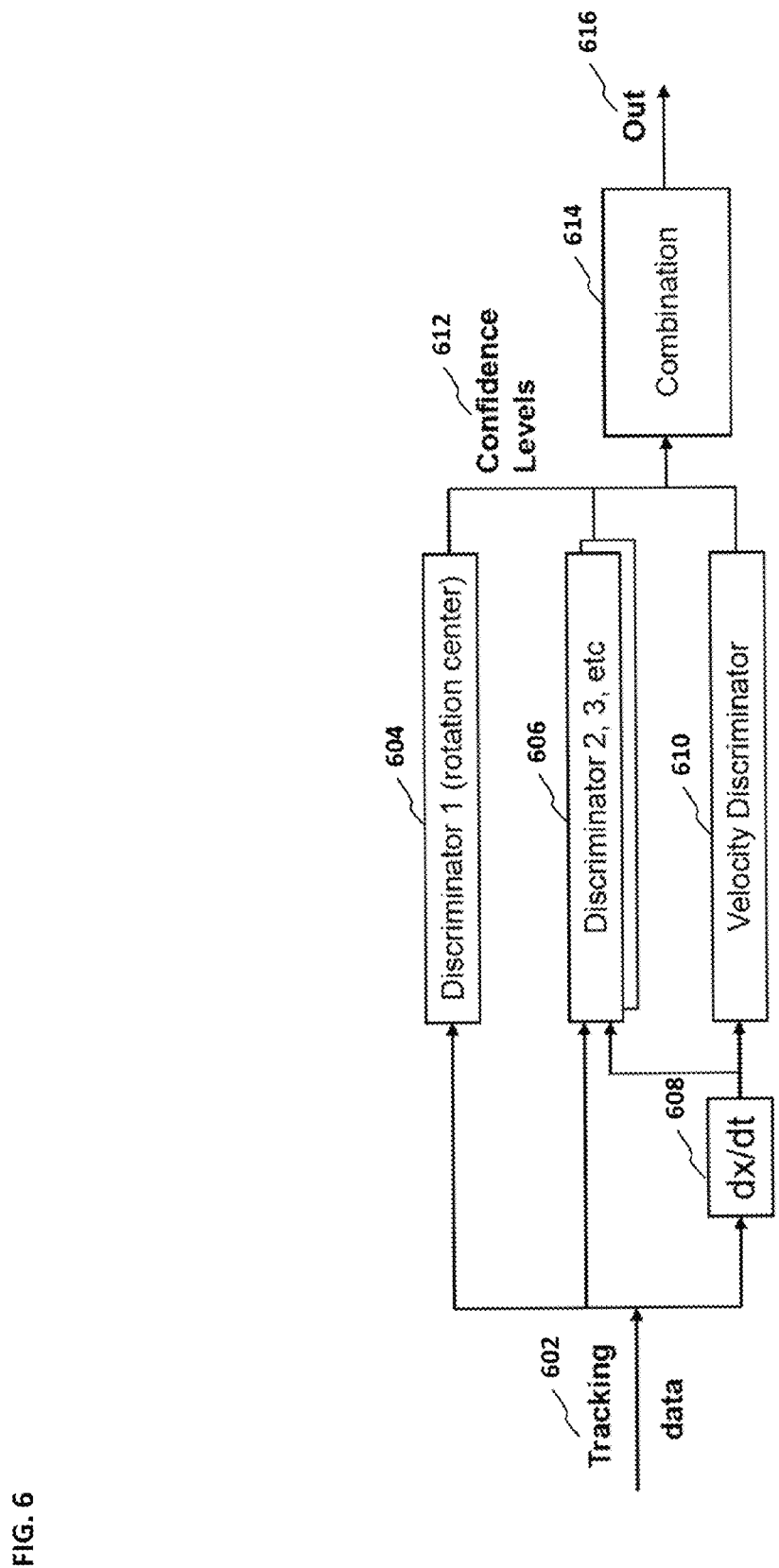
FIG. 6 is a block diagram depicting an embodiment of a complex tracking quality classifier.

In some embodiments, the system can comprise a plurality of false motion discriminators, wherein the determined confidence levels or other output of each of the false motion discriminators can be combined in some manner to generate a final output. By utilizing a plurality of false motion discriminators, the accuracy and quality of the system to detect false motions can be substantially improved. FIG. 6 is a block diagram depicting an embodiment of a complex tracking quality classifier.

As depicted in FIG. 6, in some embodiments, tracking data from one or more detectors can be collected in block 602. Such tracking data can be further analyzed by one or more false motion discriminators. For example, in some embodiments, the system can comprise a false motion discriminator that determines the likelihood of a false motion being present based on the rotation center of the movement 604. Such false motion discriminators based on rotational centers can utilize one or more processes described herein.

Further, in certain embodiments, the system can further comprise one or more additional false motion discriminators 606. For example, the one or more additional false motion discriminators 606 can utilize one or more neural or probabilistic methods or processes in determining false motion as discussed herein. In some embodiments, the system can be configured to determine first and/or second temporal derivatives of the tracked motion at block 608, which correspond to velocity and acceleration as discussed above. In certain embodiments, the one or more additional false motion discriminators 606 can be configured to utilize the determined velocity and/or acceleration data of the tracked motion in determining the likelihood of false or true motion. In other embodiments, the one or more additional false motion discriminators 606 can be configured to determine a likelihood of false or true motion without utilizing data relating to the velocity and/or acceleration of the tracked motion. In certain embodiments, one or more of a plurality of false motion discriminators can be configured to utilize velocity and/or acceleration data generated from tracked motion while other one or more of the plurality of false motion discriminators can be configured not to utilize the velocity and/or acceleration data in determining the likelihood of false and/or true motion.

In some embodiments, the system can comprise a velocity-based false motion discriminator 610 configured to determine a confidence level regarding the true or false nature of tracked motion. Any such false motion discriminator 610 configured to utilize velocity of the tracked data as basis for determining a likelihood of false motion can use any of such processes or methods described herein.

In certain embodiments, each or some subset of false motion discriminators 604, 606, 610 of the system can be configured to produce or output a confidence level 612. In some embodiments, such confidence levels 612 can be combined in block 614 according to one or more methods or processes. For example, in some embodiments, the system can comprise one or more combination modules.

The system or one or more combination modules thereof can be configured to use one or more methods to combine the one or more confidence levels. For example, the system can be configured to utilize a simple "winner takes all" process. In such embodiments, the overall probability of false marker movement can be defined as the highest confidence level value of individual discriminators, wherein a high confidence level corresponds to a high likelihood of false motion being present. Further, in certain embodiments, the system can be configured to utilize a more sophisticated approach, such as a Bayesian approach.

In some embodiments, the combination module 614 can be configured to combine the one or more confidence levels 612 and generate an output 616. The output 616 can be binary. For example, in certain embodiments, the system can be configured to generate an output of 0 when it determines that a particular movement or motion corresponds to rigid body movement and can generate an output of 1 when it determines that the movement corresponds to skin motion or false movement. In certain embodiments, if the output is 0, then the system can be configured to apply one or more motion correction processes to clarify the image. In contrast, if the output is 1, the system can be configured not to apply any motion correction process despite the fact that motion tracking data was obtained.

Complex Tracking Quality Classifier with External Input

In some embodiments, a system can comprise an additional external input in addition to the one or more false motion discriminators. The system can comprise an additional external input in order to provide an additional input or confidence level generator to further improve the accuracy of the one or more false motion discriminators. For example, in some embodiments, one or more external inputs can be configured to determine one or more external confidence levels. In certain embodiments, such one or more external confidence levels can be combined with the one or more confidence levels determined by the one or more false motion discriminators.

For example, in some embodiments where the system comprises more than one sensor to track motion, an external discriminator of the system may be configured to calculate a confidence measure based on internal consistency of data from multiple sensors. In certain embodiments, an external discriminator may be configured to detect and process acoustic noise from a patient in the medical imaging scanner or therapeutic device, since high acoustic noise levels can be associated with patient discomfort and/or pain and thus an increased probability of false marker movements. Further, in some embodiments, an external discriminator of the system can be configured to utilize video tracking to determine actual movement of the subject.

Figure 7:
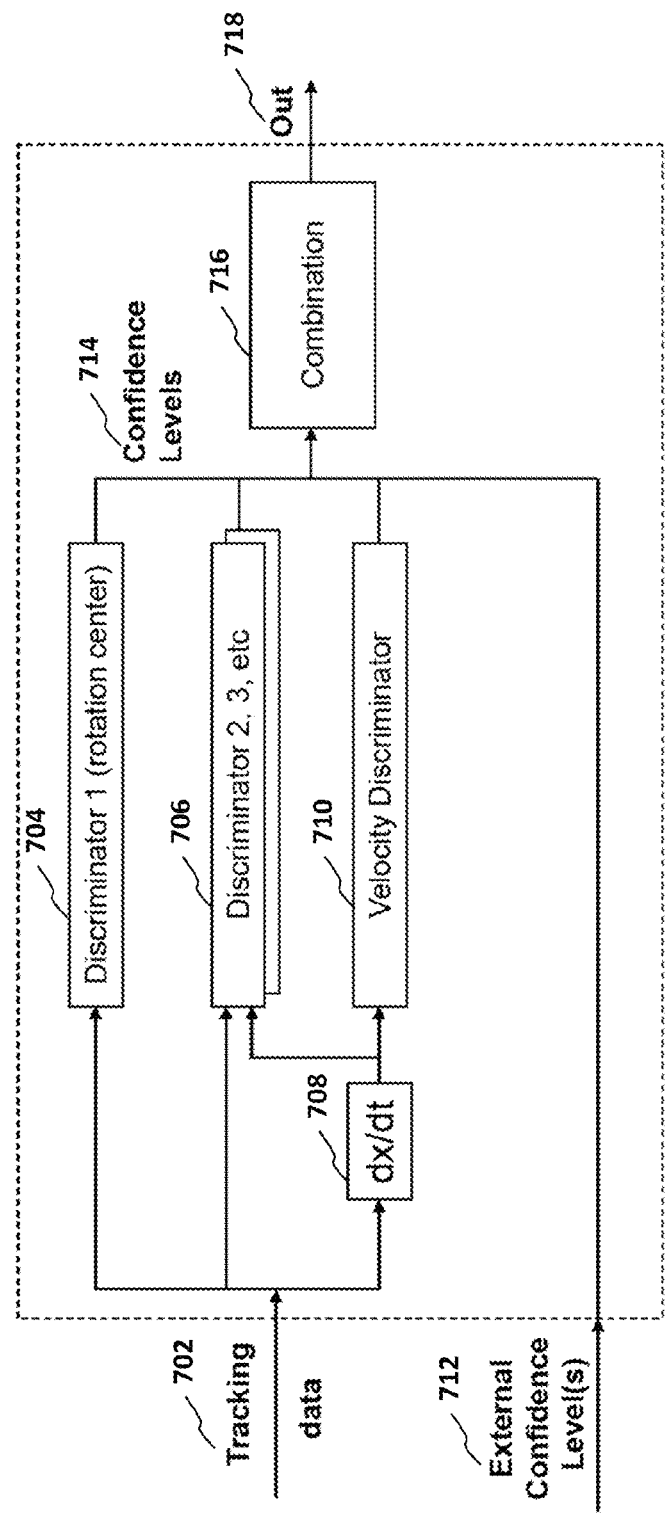
FIG. 7 is a block diagram depicting an embodiment of a complex tracking quality classifier with additional external input.

FIG. 7 is a block diagram depicting an embodiment of a complex tracking quality classifier with additional external input. As illustrated in FIG. 7, in some embodiments, the system can be configured to track motion data in block 702 using one or more sensors. The system can also comprise one or more external discriminators configured to determine one or more external confidence levels in block 712.

In some embodiments, one or more confidence levels determined by one or more false motion discriminators 704, 706, 710, utilizing one or more methods or processes described herein can then be further combined in block 716 together and with the one or more external confidence levels 712. The one or more confidence levels determined by the one or more false motion discriminators 704, 706, 710 and the one or more external discriminators can be combined based on a winner takes all process and/or a more complex statistical approach such as a Bayesian approach.

Medical Imaging Scanning System with a Tracking Quality Classifier

Figure 8:
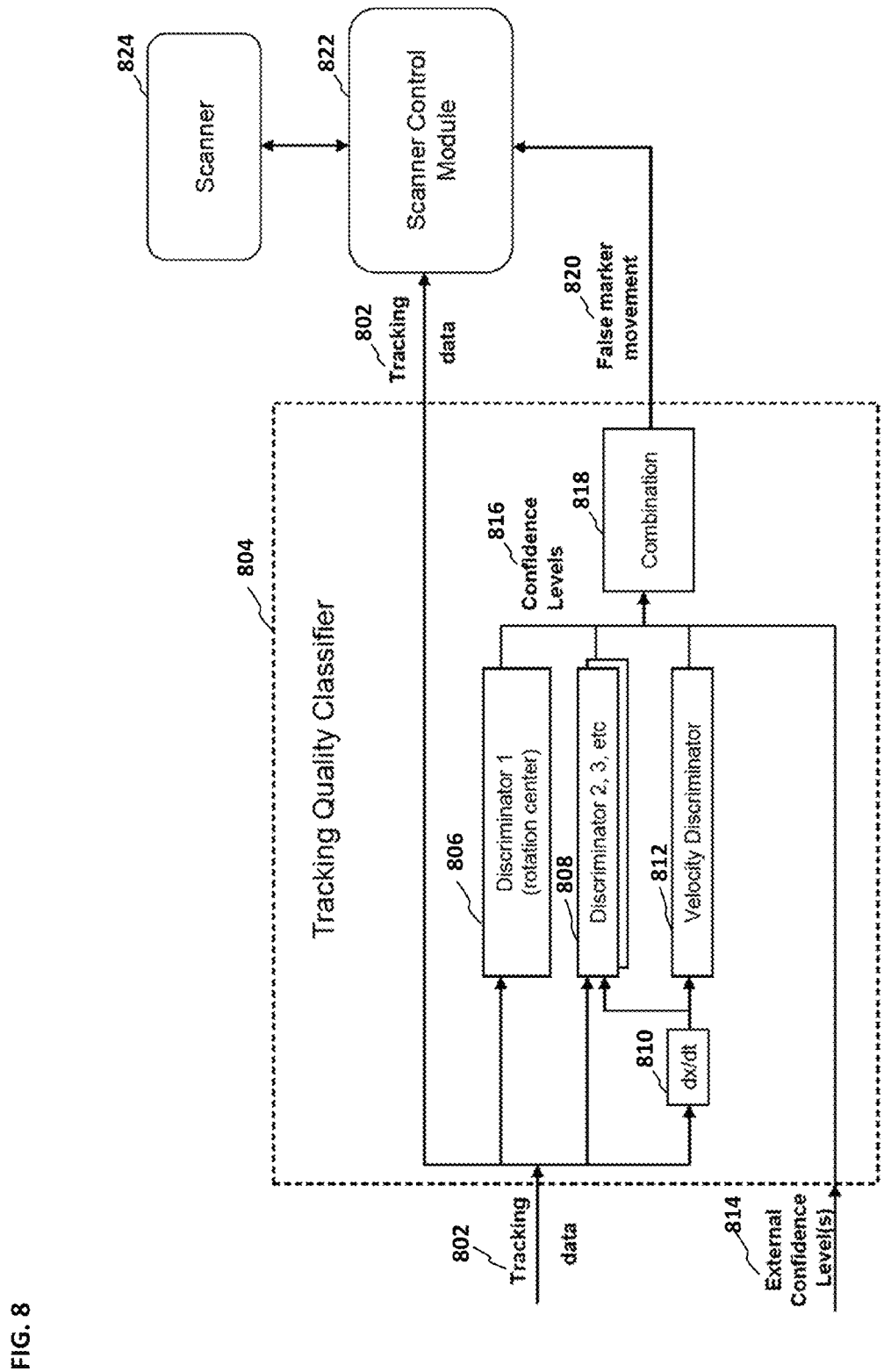
FIG. 8 is a block diagram depicting an embodiment of a biomedical or medical scanning system with a tracking quality classifier.

As discussed herein, in some embodiments, one or more tracking quality classifiers can be combined with or be part of a medical imaging scanner and/or therapeutic device or system that utilizes motion detection and/or correction systems in order to improve scan quality. FIG. 8 is a block diagram depicting an embodiment of a biomedical scanning system with a tracking quality classifier. For example, a scanner can be any medical or biomedical imaging system, such as MRI, CAT, PET, SPECT, nuclear medicine, or the like.

The acquisition of images by the scanner can be controlled by a scanner control module. In some embodiments, prospective motion correction is achieved by sending tracking data to the scanner control module, which continuously adjusts scan parameters, such as slice positions and/or rotations, such that the scan tracks motion of the object of interest. In certain embodiments, the scanner control module can be configured to additionally receive information regarding false marker movement from any one or more tracking quality classifiers as described herein.

If the false marker movement information indicates false marker movement, the system or scanner control module can be configured to take appropriate action to avoid false motion corrections. For example, in some embodiments, the scanner control module or other part or device of the system can be configured to (1) not apply motion correction updates, (2) pause image acquisition until the false marker condition has resolve, (3) acquire "dummy" or place-holder acquisitions and re-acquire real acquisitions once the condition has resolved and/or (4) apply other corrective measures.

As illustrated in FIG. 8, in some embodiments, the system can be configured to detect and/or track motion data in block 802. In certain embodiments, the system can comprise one or more external discriminators that are configured to determine one or more external confidence levels 814 as discussed above. The tracking data 802 and/or external confidence level(s) 814 can be then inputted into a tracking quality classifier 804.

In some embodiments, the tracking quality classifier 804 can comprise one or more false motion discriminators. For example, the tracking quality classifier 804 can comprise a rotation center-based false motion discriminator 806. The tracking quality classifier 804 may comprise one or more additional false motion discriminators 808. For example, the one or more additional discriminators 808 can be configured to detect or determine false motion based on a neural network and/or via a probabilistic process. In certain embodiments, the one or more additional discriminators 808 can be configured to determine or detect false motion based on velocity 810 and/or acceleration of the tracked data.

In certain embodiments, the tracking quality classifier 804 can be configured to determine a first order temporal derivative 810 and/or second or higher order temporal derivatives. In some embodiments, the tracking quality classifier 804 can comprise a velocity-based false motion discriminator 812.

Confidence levels 816 determined by the one or more false motion discriminators and/or one or more external confidence levels 814 can be combined in block 818. For example, the combination may involve a winner takes all approach and/or statistical approach, such as a Bayesian process.

If the tracking quality classifier 804 determines that false movement or false marker movement was likely present for a particular period of time, the system can be configured to transmit the false marker movement related data 820 and the tracking data 802 of that period to a scanner control module 822. The scanner control module 822 can be configured to respond utilizing any of the methods discussed above in controlling the scanner 824.

False Motion Classifier with Differential Motion Discriminator

As discussed above, in some embodiments, a motion detection and/or correction system for a medical imaging scanner and/or therapeutic device can comprise one or more markers or trackers. For such systems, in certain embodiments, a false motion classifier or tracking quality classifier can comprise one or more differential motion discriminators. Such differential motion discriminators can be configured to track the motion of two or more markers relative to each other and utilize such data to determine whether rigid body movement or facial movement or false movement was involved.

Figure 9:
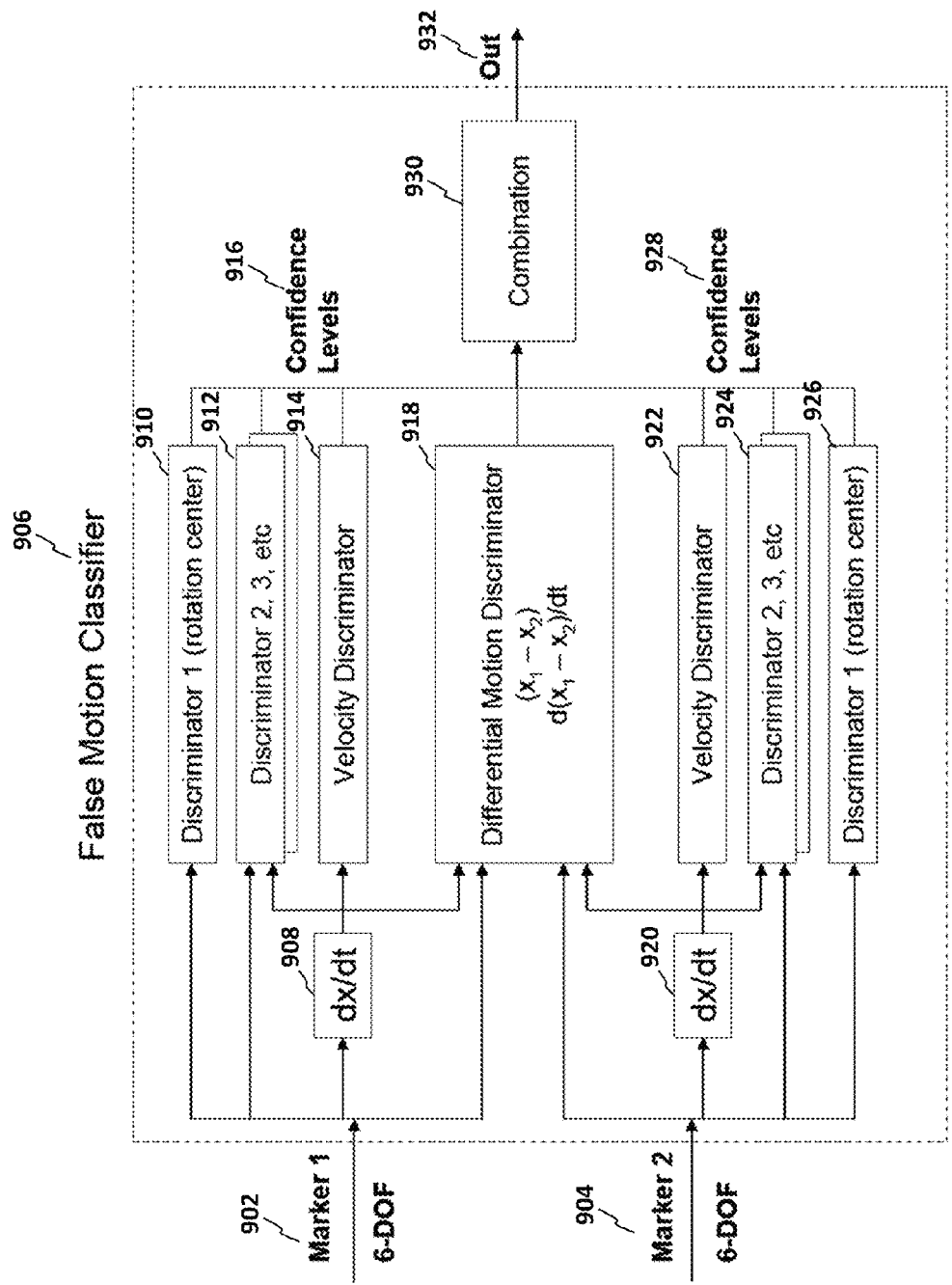
FIG. 9 is a block diagram depicting an embodiment of a complex tracking quality classifier with a differential motion discriminator.

FIG. 9 is a block diagram depicting an embodiment of a complex tracking quality classifier with a differential motion discriminator. In some embodiments, as illustrated in FIG. 9, a motion detection and/or correction system to be used in conjunction with a medical imaging scanner and/or therapeutic device or system can involve use of one or more markers 902, 904. Such markers can be configured to provide 6 degrees of freedom in some embodiments. In certain embodiments, in addition to the one or more false motion discriminators 910, 912, 914, 922, 924, 926, which can involve any one or more methods of processes described herein, the false motion classifier 906 can further comprise a differential motion discriminator 918.

A differential motion discriminator 918 can be configured to detect and/or track movement or motion of the plurality of markers 902, 904 relative to each other. For example, the differential motion discriminator 918 can be configured to determine the distance and/or relative location of two or more markers 902, 904 relative to each other. In certain embodiments, the differential motion discriminator 918 can further be configured to determine a first order and/or second order temporal derivative of the relative location of the two or more markers 902, 904 to determine a velocity and/or acceleration of movement of the two or more markers 902, 904 relative to each other. The basic assumption can be that when a rigid body movement occurs, all or substantially all markers located on the subject move together, thereby not moving or substantially not moving relative to each other. However, when skin movement or false movement occurs, the location of one or more markers relative to others can change, rather abruptly in certain circumstances.

As such, in some embodiments, the system can be configured to determine that a high likelihood of false movement is present when the relative movement between two or more markers present on a subject is above a certain threshold, percentage, or ratio. Similarly, in certain embodiments, the system can be configured to determine that a high likelihood of false movement is present when a first order temporal derivative of relative location of two or more markers or velocity of relative movement is above a certain threshold, percentage, or ratio.

In certain embodiments, the differential motion discriminator 918 can be configured to generate a confidence level 916, 918 similar to those discussed above. In some embodiments, confidence levels 916 determined by one or more false movement discriminators 910, 912, 914 with respect to a first marker 902, confidence levels 918 determined by one or more false movement discriminators 922, 924, 926 with respect to a second marker 904, and/or a confidence level determined by a differential motion discriminator 918 based on both the first and second markers 902, 904 can be combined in block 930 using any of the combination methods or process discussed herein. Further, the system can be configured to generate one or more outputs, such as a binary output as discussed above in block 932.

In some embodiments, the differential motion discriminator 918 may provide the highest overall accuracy compared to the other false motion discriminators based on a single marker. However, for systems that utilize only a single marker, other false motion discriminators configured to determine false motion based on tracking data provided by a single marker may be important. Further, since false-negative events, where false tracking is not detected, but not false-positive events, may cause deterioration of MRI scan quality, it can be important to minimize the false-negative rate. The false-negative rate can be minimized by optimizing one or more thresholds for the one or more false motion discriminators.

Variations

Specific embodiments have been described in detail above with emphasis on medical application and in particular MRI examination of a patient's head. However, the teachings of the present invention can be utilized for other MRI examinations of other body parts where movements of up to six degrees of freedom are possible. In addition medical procedures involving imaging devices other than MRI equipment (e.g., CT, PET, ultrasound, plain radiography, and others) may benefit from the teaching of the present invention. The teachings of the present invention may be useful in many non-medical applications where tracking of a target having several degrees of freedom are possible. Some of these applications could be military applications. Furthermore, while particular algorithms are disclosed, variations, combinations, and subcombinations are also possible.

Computing System

Figure 10:
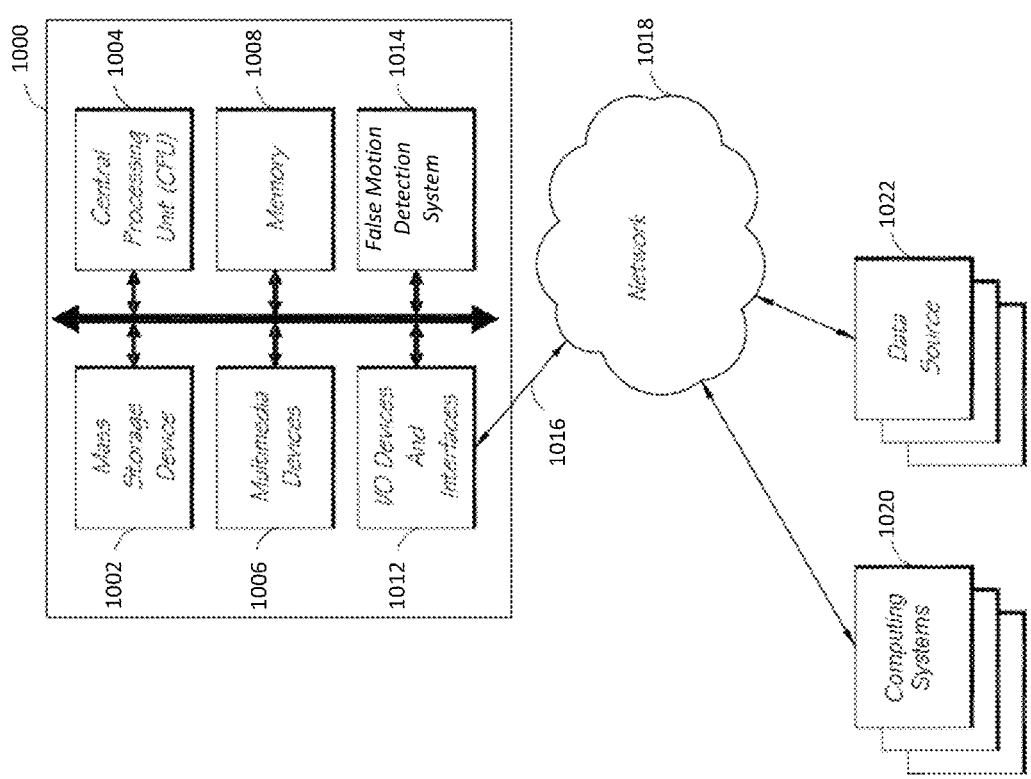
FIG. 10 is a block diagram depicting an embodiment of a computer system configured to implement one or more embodiments of the methods, devices, and systems described herein.

In some embodiments, the computer clients and/or servers described above take the form of a computing system illustrated in FIG. 10, which is a block diagram of one embodiment of a computing system that is in communication with one or more computing systems 1020 and/or one or more data sources 1022 via one or more networks 1018. The computing system 1000 may be used to implement one or more of the systems and methods described herein. In addition, in one embodiment, the computing system 1000 may be configured to apply one or more of the methods and systems described herein. While FIG. 10 illustrates an embodiment of a computing system 1000, it is recognized that the functionality provided for in the components and modules of computing system 1000 may be combined into fewer components and modules or further separated into additional components and modules.

False Motion Detection System

In an embodiment, the system 1000 comprises a false motion detection system module 1014 that carries out the functions described herein with reference to false motion detection, including any one of the false motion detection and/or combination methods described above. The false motion detection system module 1014 may be executed on the computing system 1000 by a central processing unit 1004 discussed further below.

In general, the word "module," as used herein, refers to logic embodied in hardware or firmware, or to a collection of software instructions, possibly having entry and exit points, written in a programming language, such as, for example, COBOL, CICS, Java, Lua, C or C++ or Objective C. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

Computing System Components

In an embodiment, the computing system 1000 also comprises a workstation or other computing devices suitable for controlling and/or communicating with large databases, performing transaction processing, and generating reports from large databases. The computing system 1000 also comprises a central processing unit ("CPU") 1004, which may comprise a conventional microprocessor. The computing system 1000 further comprises a memory 1008, such as random access memory ("RAM") for temporary storage of information and/or a read only memory ("ROM") for permanent storage of information, and a mass storage device 1002, such as a hard drive, diskette, or optical media storage device. Typically, the modules of the computing system 100 are connected to the computer using a standards based bus system. In different embodiments, the standards based bus system could be Peripheral Component Interconnect (PCI), Microchannel, SCSI, Industrial Standard Architecture (ISA) and Extended ISA (EISA) architectures, for example.

The computing system 1000 comprises one or more commonly available input/output (I/O) devices and interfaces 1012, such as a keyboard, mouse, touchpad, and printer. In one embodiment, the I/O devices and interfaces 1012 comprise one or more display devices, such as a monitor, that allows the visual presentation of data to a user. More particularly, a display device provides for the presentation of GUIs, application software data, and multimedia presentations, for example. In the embodiment of FIG. 10, the I/O devices and interfaces 1012 also provide a communications interface to various external devices. The computing system 1000 may also comprise one or more multimedia devices 1006, such as speakers, video cards, graphics accelerators, and microphones, for example.

Computing System Device/Operating System

The computing system 1000 may run on a variety of computing devices, such as, for example, a mobile device or a server or a desktop or a workstation, a Windows server, an Structure Query Language server, a Unix server, a personal computer, a mainframe computer, a laptop computer, a cell phone, a personal digital assistant, a kiosk, an audio player, a smartphone, a tablet computing device, and so forth. The computing system 1000 is generally controlled and coordinated by operating system software, such as iOS, z/OS, Windows 95. Windows 98, Windows NT, Windows 2000, Windows XP, Windows Vista, Windows 7, Linux, BSD, SunOS, Solaris, or other compatible operating systems. In Macintosh systems, the operating system may be any available operating system, such as MAC OS X. In other embodiments, the computing system 1000 may be controlled by a proprietary operating system. Conventional operating systems control and schedule computer processes for execution, perform memory management, provide file system, networking, and I/O services, and provide a user interface, such as a graphical user interface ("GUI"), among other things.

Network

In the embodiment of FIG. 10, the computing system 1000 is coupled to a network 1018, such as a LAN, WAN, or the Internet, for example, via a wired, wireless, or combination of wired and wireless, communication link 1016. The network 1018 communicates with various computing devices and/or other electronic devices via wired or wireless communication links. In the embodiment of FIG. 10, the network 1018 is communicating with one or more computing systems 1020 and/or one or more data sources 1022.

Access to the motion correction control system module 1014 of the computer system 1000 by computing systems 1020 and/or by data sources 1022 may be through a web-enabled user access point such as the computing systems' 1020 or data source's 1022 personal computer, cellular phone, laptop, or other device capable of connecting to the network 1018. Such a device may have a browser module is implemented as a module that uses text, graphics, audio, video, and other media to present data and to allow interaction with data via the network 1018.

The browser module may be implemented as a combination of an all points addressable display such as a cathode-ray tube (CRT), a liquid crystal display (LCD), a plasma display, touch screen display or other types and/or combinations of displays. In addition, the browser module may be implemented to communicate with input devices 1012 and may also comprise software with the appropriate interfaces which allow a user to access data through the use of stylized screen elements such as, for example, menus, windows, dialog boxes, toolbars, and controls (for example, radio buttons, check boxes, sliding scales, and so forth). Furthermore, the browser module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

In some embodiments, the system 1000 may comprise a physical or logical connection established between a remote microprocessor and a mainframe host computer for the express purpose of uploading, downloading, or viewing interactive data and databases on-line in real time. The remote microprocessor may be operated by an entity operating the computer system 1000, including the client server systems or the main server system, an/or may be operated by one or more of the data sources 1022 and/or one or more of the computing systems. In some embodiments, terminal emulation software may be used on the microprocessor for participating in the micro-mainframe link.

In some embodiments, computing systems 1020 that are internal to an entity operating the computer system 1000 may access the motion correction control system module 1014 internally as an application or process run by the CPU 1004.

User Access Point

In an embodiment, the computing system 1000 comprises a computing system, a smartphone, a tablet computing device, a mobile device, a personal computer, a laptop computer, a portable computing device, a server, a computer workstation, a local area network of individual computers, an interactive kiosk, a personal digital assistant, an interactive wireless communications device, a handheld computer, an embedded computing device, or the like.

Other Systems

In addition to the systems that are illustrated in FIG. 10, the network 1018 may communicate with other data sources or other computing devices. The computing system 1000 may also comprise one or more internal and/or external data sources. In some embodiments, one or more of the data repositories and the data sources may be implemented using a relational database, such as DB2, Sybase, Oracle, Code- Base and Microsoft® SQL Server as well as other types of databases such as, for example, a signal database, object-oriented database, and/or a record-based database.

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 3 mm" includes "3 mm."

The headings provided herein, if any, are for convenience only and do not necessarily affect the scope or meaning of the devices and methods disclosed herein.

Appendix A

Determining center of rotation for a given rigid body transformation:

A given rigid body transformation, defined by a translation (vector $a$) and rotation (matrix $R$), will move a point $x$ to point $x'$, as follows:

$$x' = a + R x \qquad (1)$$

At the center of rotation, $x$ will be invariant under this transformation, i.e.:

$$x = a + R x \qquad (2)$$

The goal of the method is to determine $x$ given a known $a$ and $R$.

---

Lemma 1: Eq. 2 provides a meaningful solution only for vectors $x$ and $a$ that are orthogonal to the rotation axis $r$.

Proof: split both $x$ and $a$ into two components, one parallel and one orthogonal to $r$:

$$x = x^\| + x^\perp \quad \text{and} \quad a = a^\| + a^\perp \qquad (3)$$

and insert into (2):

$$x^\| + x^\perp = a^\| + a^\perp + R(x^\| + x^\perp) = (a^\| + x^\|) + (a^\perp + R x^\perp) \qquad (4)$$

where the right side of Eq. (4) is rearranged to group terms that are parallel and orthogonal to the rotation axis. Note: $R x^\perp$ represents rotation of a vector orthogonal to the axis, and is therefore orthogonal to the axis as well.
Consequently, Eq. 4 can be split into two separate equations, as follows:

$$x^\| = (a^\| + x^\|) \qquad (5a)$$
$$x^\perp = (a^\perp + R x^\perp) \qquad (5b)$$

Eq. 5a yields $a^\| = 0$, i.e. requires that the translation $a^\|$ parallel to the rotation axis has to be zero, in which case any vector $x^\|$ will provide the trivial solution. Therefore, only components orthogonal to the rotation axis provide a non-trivial solution (proving the lemma).

---

For the rest of the paper, we substitute $x_0 = x^\perp$, which yields $$x_0 = a^\perp + R x_0 \qquad (6)$$

based on Eq. 5b, and in analogy to Eq. 2.

The Figure shows a graphic representation of Eq. 6 in a plane perpendicular to the rotation axis. Starting with an (unknown) vector $x_0$ and its (unknown) rotated counterpart $R\, x_0$ (rotation angle $\varphi$), then $a^\perp$ is the vector that connects $R\, x_0$ and $x_0$ on a circle of radius $|x_0|$. Based on this geometric representation, we note the following properties for vectors $a^\perp$ and $x_0$.

First, for small rotations $\varphi$, vector $a^\perp$ will be a tangent of the circle, and therefore be (approximately) orthogonal to $x_0$:

$$x_0 \cdot a^\perp \sim 0 \qquad (7)$$

Second, for small rotations $\varphi$, the length of vector $a^\perp$ will approximate the length of the circle segment defined by $a$, yielding:

$$|a^\perp| \sim |x_0| \cdot \varphi \qquad (8)$$

with $\varphi$ in rads, or $$|x_0| \sim |a^\perp| / \varphi \qquad (9)$$

SUMMARY

Starting with a translation (vector $a$) and rotation (matrix $R$), describing head movement at a given time, the center of rotation can be estimated based on 2 simple steps:

STEP 1: calculate the component $a^\perp$ of the translation vector $a$ that is orthogonal to the rotation axis (Eq. 3).

STEP 2: calculate the cross product of $a^\perp$ and the rotation axis $r$ (where $|r|=1$), and divide by the total rotation angle $\varphi$:

$$x_0 = (a^\perp \times r) / \varphi \qquad (10)$$

Note: it is trivial to demonstrate that $x_0$ as defined by Eq. 10 is i) orthogonal to both $a^\perp$ and $r$ (as required by Eqs. 3 and 7), and ii) meets Eq. 9 for $|r|=1$.

*Finally, the most common head rotations in the MRI environment are about the x-axis and z-axis. For both of these types of motion, one should be able to determine reasonable estimates of the y-coordinate of the rotation center, which seems most promising in differentiating true head movement from false skin movements.*

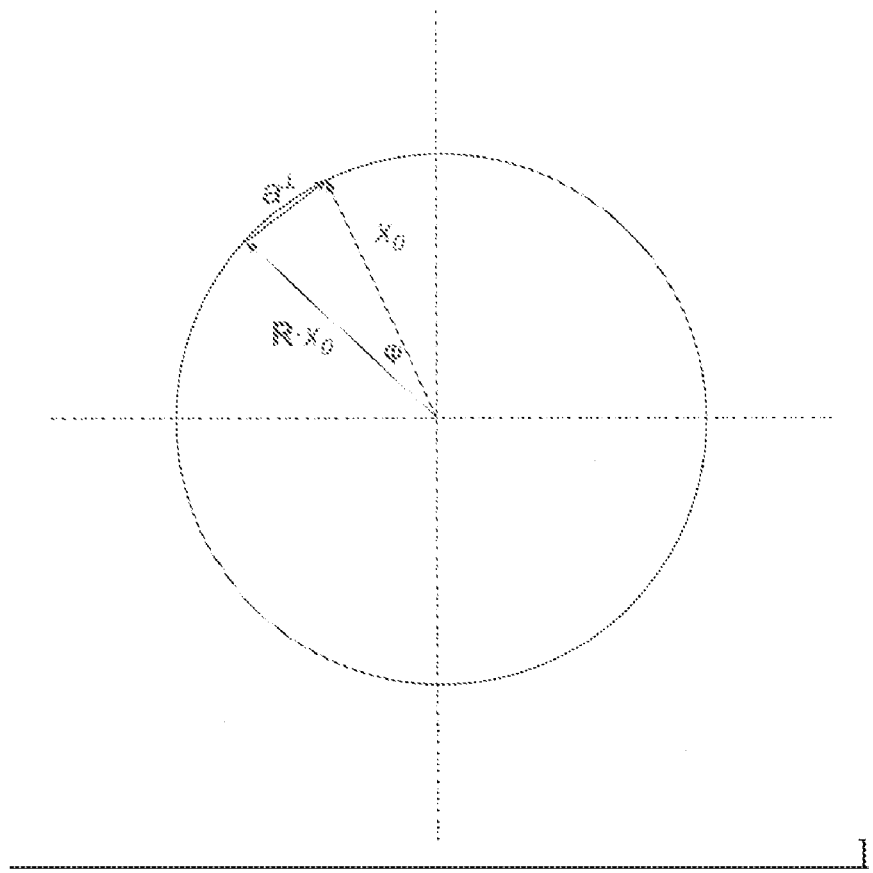

What is claimed is:

1. A computer-implemented method for determining false motion tracked by a motion correction system during a medical imaging scan, the method comprising:
   obtaining tracking data, wherein the tracking data reflects motion of a subject of the medical imaging scan or a portion thereof;
   determining by a false motion discriminator a likelihood of the obtained tracking data reflecting false motion, wherein the false motion is not reflective of true motion of the subject of the medical imaging scan or the portion thereof; and
   generating by the false motion discriminator a confidence level of the determined likelihood of the obtained tracking data reflecting false motion, wherein the motion correction system is configured to adjust output based on the confidence level,
   wherein the false motion discriminator comprises a computer processor and an electronic storage medium.

2. The computer-implemented method of claim 1, wherein the likelihood of the obtained tracking data reflecting false motion is based on at least one of velocity, acceleration, center of rotation, and axis of rotation of the motion of the subject.

3. The computer-implemented method of claim 1, wherein the likelihood of the obtained tracking data reflecting false motion is based on machine learning.

4. A false motion classifier system for determining false motion tracked by a motion correction system during a medical imaging scan, the false motion classifier system comprising:
   a first false motion discriminator configured to determine a center of rotation of a detected motion and further determine a first confidence level based on the center of rotation of the detected motion, wherein the first confidence level is indicative of the detected motion being true or false;
   a second false motion discriminator configured to determine a velocity of the detected motion and further determine a second confidence level based on the velocity of the detected motion, wherein the second confidence level is indicative of the detected motion being true or false; and
   a combination module configured to combine the first and second confidence levels to generate an output indicative of the detected motion being true or false, wherein an output indicative of the detected motion being false causes the motion correction system not to apply one or more motion correction processes to the detected motion.

5. The false motion classifier system of claim 4 further comprising a third false motion discriminator configured to determine a third confidence level indicative of the detected motion being true or false based on machine learning.

6. The false motion classifier system of claim 4 further comprising a differential motion discriminator configured to determine a third confidence level indicative of the detected motion being true or false based on relative motion of two or more motion trackers used by the motion correction system.

7. The false motion classifier system of claim 4 further comprising one or more external discriminators configured to determine one or more external confidence levels indicative of the detected motion being true or false.

8. The false motion classifier system of claim 7, wherein the one or more external discriminators are configured to determine the one or more external confidence levels based on at least one or more of noise and video tracking.

9. The false motion classifier system of claim 4, wherein the output is binary.

10. A motion correction system for detecting and correcting motion by a subject during a medical imaging scan, the motion correction system comprising:
    one or more markers placed on one or more portions of the subject;
    one or more detectors configured to track motion of the one or more markers; and
    a tracking quality classifier for determining false motion of the one or more markers, wherein the tracking quality classifier system comprises one or more false motion discriminators,
    wherein determination by the tracking quality classifier that a false motion of the one or more markers occurred causes the motion correction system not to apply one or more motion correction processes to the false motion.

11. The motion correction system of claim 10, wherein the one or more false motion discriminators are configured to determine false motion of the one or more markers based on at least one or more of velocity, rotational center, and machine learning.

12. The motion correction system of claim 10, wherein the tracking quality classifier further comprises one or more external discriminators.

13. The motion correction system of claim 10, further comprising a scanner control module configured to control a scanner for the medical imaging scan not to utilize acquired data during the false motion.

14. The motion correction system of claim 10, further comprising a scanner control module configured to control a scanner for the medical imaging scan to repeat acquisitions of data initially acquired during the false motion.

* * * * *